US012696857B2

(12) United States Patent
De et al.

(10) Patent No.: US 12,696,857 B2
(45) Date of Patent: Aug. 4, 2026

(54) PLANT MANAGEMENT SYSTEM AND DEVICE

(71) Applicant: FloraSense Inc., Chicago, IL (US)

(72) Inventors: Aabesh De, Chicago, IL (US);
Mauricio Adrián Villalobos Casares,
Merida (MX); Ayrton Estrella Alcocer,
Merida (MX)

(73) Assignee: FloraSense Inc., Cordova, TN (US)

( * ) Notice: Subject to any disclaimer, the term of this
patent is extended or adjusted under 35
U.S.C. 154(b) by 1151 days.

(21) Appl. No.: 17/717,705

(22) Filed: Apr. 11, 2022

(65) Prior Publication Data

US 2023/0200317 A1 Jun. 29, 2023

Related U.S. Application Data

(60) Provisional application No. 63/294,150, filed on Dec.
28, 2021.

(51) Int. Cl.
| | |
|---|---|
| *A01G 25/16* | (2006.01) |
| *A01G 9/24* | (2006.01) |
| *G01N 33/24* | (2006.01) |
| *G06N 3/045* | (2023.01) |
| *G06N 3/084* | (2023.01) |

(52) U.S. Cl.
CPC ............. *A01G 25/167* (2013.01); *A01G 9/24*
(2013.01); *G01N 33/245* (2024.05); *G06N
3/045* (2023.01); *G06N 3/084* (2013.01)

(58) Field of Classification Search
CPC .......... A01G 25/167; A01G 9/24; A01G 7/00;
G01N 33/245; G06N 3/045; G06N 3/084;
G06N 3/0464
See application file for complete search history.

(56) References Cited

U.S. PATENT DOCUMENTS

| | | | |
|---|---|---|---|
| 5,458,093 | A | 10/1995 | MacMillan |
| 8,340,910 | B1 | 12/2012 | Magro et al. |
| 8,528,834 | B2 | 9/2013 | Skinner |
| 9,271,454 | B1 | 3/2016 | Shochat et al. |
| 10,219,431 | B2 | 3/2019 | Stoller et al. |
| 10,921,303 | B1 | 2/2021 | Dong et al. |
| 10,986,789 | B1 * | 4/2021 | Roberts ................... A01G 9/26 |
| 11,266,081 | B2 | 3/2022 | Lys et al. |
| 2002/0024445 | A1 | 2/2002 | Takayama et al. |
| 2011/0000131 | A1 | 1/2011 | Chan et al. |
| 2015/0164009 | A1 | 6/2015 | Chandran et al. |
| 2016/0266570 | A1 | 9/2016 | So |
| 2017/0270817 | A1 | 9/2017 | Kasravi et al. |

(Continued)

*Primary Examiner* — Manuel A Rivera Vargas
(74) *Attorney, Agent, or Firm* — IDP Patent Services;
Olav M. Underdal

(57) ABSTRACT

A plant management system, includes: a plant management
server, including a plant id manager, a plant reference
database with plant reference records, and a micro-climate
manager; at least one plant management sensor device,
including a moisture sensor, a temperature and humidity
sensor, and a light sensor; and a plant management control
device, including: a plant controller, and a micro-climate
controller; such that the plant management control device is
configured to enable a user to control and view sensor data,
from at least one plant management sensor device, which
can measure ambient temperature, ambient humidity, ambi-
ent light, and soil moisture of the soil.

26 Claims, 33 Drawing Sheets

System for Plant Management

Plant User Database

(56) References Cited

U.S. PATENT DOCUMENTS

| | | | |
|---|---|---|---|
| 2018/0000025 A1 | 1/2018 | He et al. | |
| 2018/0014455 A1 | 1/2018 | Zielke | |
| 2018/0262571 A1 | 9/2018 | Akhtar | |
| 2018/0295783 A1 | 10/2018 | Alexander et al. | |
| 2021/0100173 A1* | 4/2021 | Khwaja | A01G 9/24 |
| 2021/0289724 A1 | 9/2021 | Chavez | |
| 2021/0315168 A1* | 10/2021 | Readick | F24S 23/70 |
| 2024/0219938 A1* | 7/2024 | Zhang | G05D 22/02 |

* cited by examiner

System for Plant Management

Plant Management Sensor Device

Plant Management Server

Plant Reference Database

Plant User Database

Plant Management Control Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Plant Management Sensor Device

Main Headpiece Body

620

626

622

624

625

620

622

626

624

625

1030

104

PLANT MANAGEMENT SYSTEM AND DEVICE

CROSS-REFERENCE TO RELATED APPLICATIONS

This US Non-Provisional application claims the benefit of U.S. Provisional Application No. 63/294,150, filed Dec. 28, 2021; which is hereby incorporated herein by reference in its entirety.

FIELD OF THE INVENTION

The present invention relates generally to the field of plant management, and more particularly to methods and systems for plant identification and control of a plant environment.

BACKGROUND OF THE INVENTION

Gardening and plant keeping is a popular activity, wherein people may maintain plants both outside, in their garden or yard, as well as inside, typically with potted plants.

However, many amateur gardeners may find themselves unable to identify all their plants and may also have trouble determining and controlling an appropriate grow environment for their plants.

As such, considering the foregoing, it may be appreciated that there continues to be a need for novel and improved devices and methods for plant identification and control of a garden environment.

SUMMARY OF THE INVENTION

The foregoing needs are met, to a great extent, by the present invention, wherein in aspects of this invention, enhancements are provided to the existing model of plant identification and control of a garden environment.

In an aspect, a plant management system, can include:
- a) a plant management server;
- b) a plant management control device; and
- c) a plant management sensor device, wherein the plant management sensor device can be positioned in proximity to plant, which is planted in a soil of a garden bed or planting pot;
- such that the plant management control device can enable a user to control and view sensor data, from at least one plant management sensor device, which can measure ambient temperature, ambient humidity, ambient light, and soil moisture of the soil.

In a related aspect, the plant management sensor device can include:
- a) A processor, which can be a microcontroller, which can have Wi-Fi and/or Bluetooth connectivity;
- b) A non-transitory memory;
- c) An input/output;
- d) a moisture sensor;
- e) A temperature and humidity sensor;
- f) A light sensor; and
- g) A charging port;
- h) A battery charger;
- i) A rechargeable battery;
- j) A voltage supervisor;
- k) A voltage regulator;
- l) A programming port; and
- m) At least one user button; all connected via
- n) A data bus.

In another related aspect, the plant management server can include:
- a) A processor;
- b) A non-transitory memory;
- c) An input/output component;
- d) A plant id manager, which can be configured to identify a plant species, based on a plant actual image, which is captured by a camera of the plant management control device;
- e) A plant reference database, which comprises a library of plant information, wherein the plant reference database can include:
  - i. a plurality of plant reference records;
  - wherein the plant id manager can be configured to identify the plant actual image to match a plant reference images by a search in the plant reference database; and
- f) A micro-climate manager, which is configured to capture, store, and process local climate information from the at least one plant management sensor device; all connected via
- g) A data bus;

In a further related aspect, the plant reference database can include a plurality of plant reference records, each including:
- a) A plant description;
- b) A plant temperature range;
- c) A plant light exposure range;
- d) A plant soil descriptor, which can include
  - i. a plant soil moisture range; and
  - ii. a plant soil type;
- e) A plant nutrient descriptor, which can include
  - i. a plant fertilization mix; and
  - ii. a plant fertilization quantity; and
- f) Images, which can include:
  - i. at least one plant reference image;

In a related embodiment, the plant management control device, can include:
- a) A processor;
- b) A non-transitory memory;
- c) An input/output;
- d) A plant controller, which is configured to view and process plant information, received from the plant reference database, in communication via the plant management server; and
- e) A micro-climate controller, which is configured to view and process climate information, received from:
  - i. the plant reference database, in communication via the plant management server; and/or
  - ii. the at least one plant management sensor device, either in direct communication between the plant management control device and the at least one plant management sensor device or via the plant management server; all connected via
- f) A data bus.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
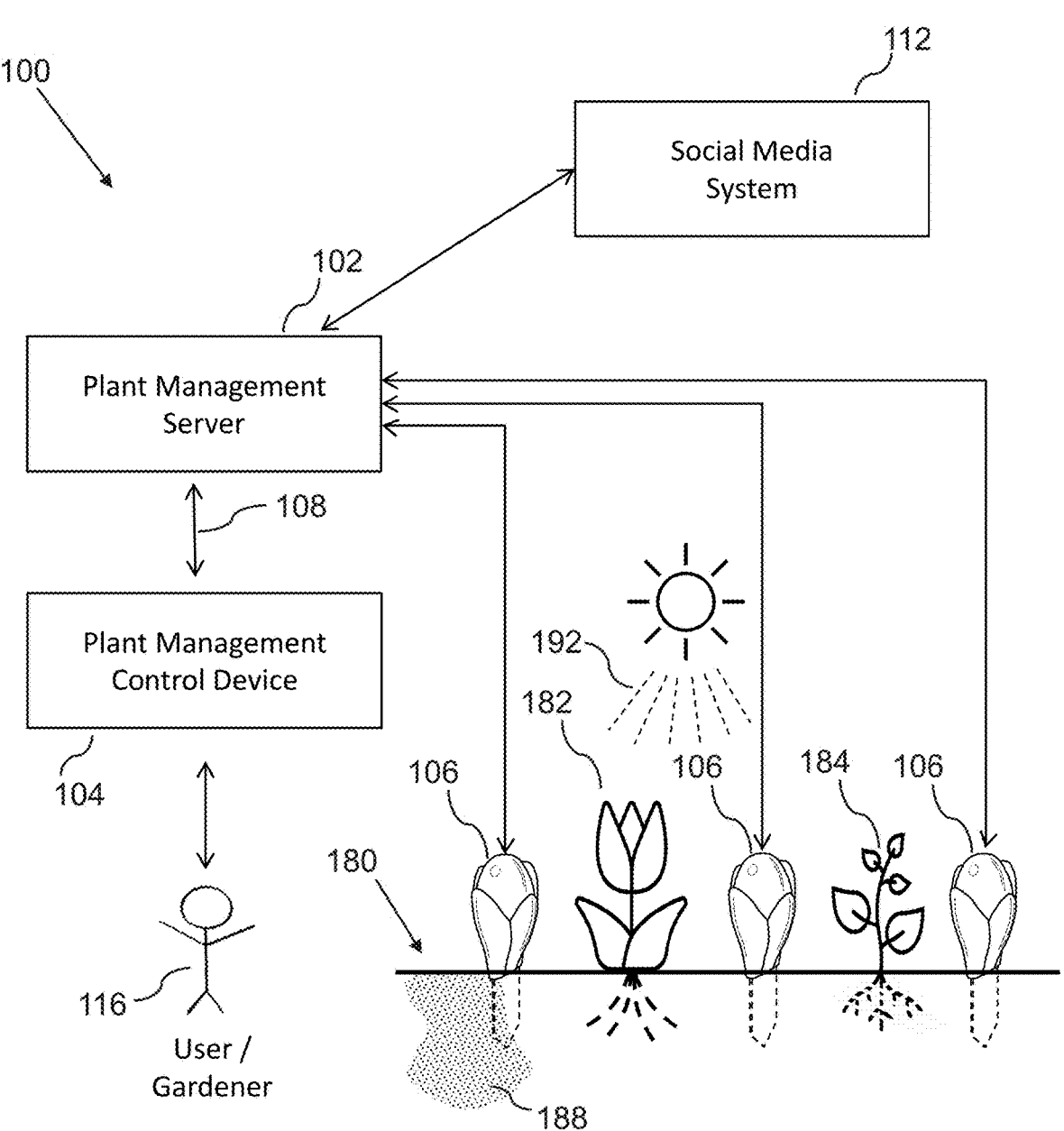
FIG. 1 is a schematic diagram illustrating the plant management system according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of the plant management system 100 with reference to FIG. 1, in such manner that like reference numerals refer to like components throughout; a convention that we shall employ for the remainder of this specification.

In an embodiment, as shown in FIG. 1, a plant management system 100, can include:

a) a plant management server 102;

b) a plant management control device 104; and c) a plant management sensor device 106, wherein the plant management sensor device 106 can be positioned in proximity to at least one plant 182, 184, which is planted in a planting soil 188 of a garden bed 180 or planting pot;

such that the plant management control device 104 can enable a user to control and view sensor data, from at least one plant management sensor device 106, which can measure ambient temperature, ambient light, and soil moisture of the planting soil 188.

In a related embodiment, as shown in FIGS. 2A-2B, 6D, 9A, and 9D-9F, an electronics assembly 954 of a PCB assembly 650 of the plant management sensor device 106, can include:

a) A processor 202, which can be a microcontroller, which can have Wi-Fi and/or Bluetooth connectivity;

b) A non-transitory memory 204;

c) An input/output 206;

d) a moisture sensor circuit 208, which can also be referred to as a moisture sensor 208, which can include:

i. at least one moisture probe 209, which can be configured as a copper probe node 209; or plurality of moisture probes 209;

e) A temperature and humidity sensor circuit 210;

f) A light sensor circuit 212;

g) A charging port 220;

h) A battery charger 222;

i) A battery 224, which can be a rechargeable lithium-ion polymer battery;

j) At least one voltage supervisor 226, which monitors power supplied to the onboard microcontroller 202;

k) A voltage regulator 228, which regulates power supplied to the onboard microcontroller 202, and other electronic components, such as LEDs 229;

l) A programming port 230; and m) At least one user button 232; all connected via n) A data bus 240.

Figure 3A:
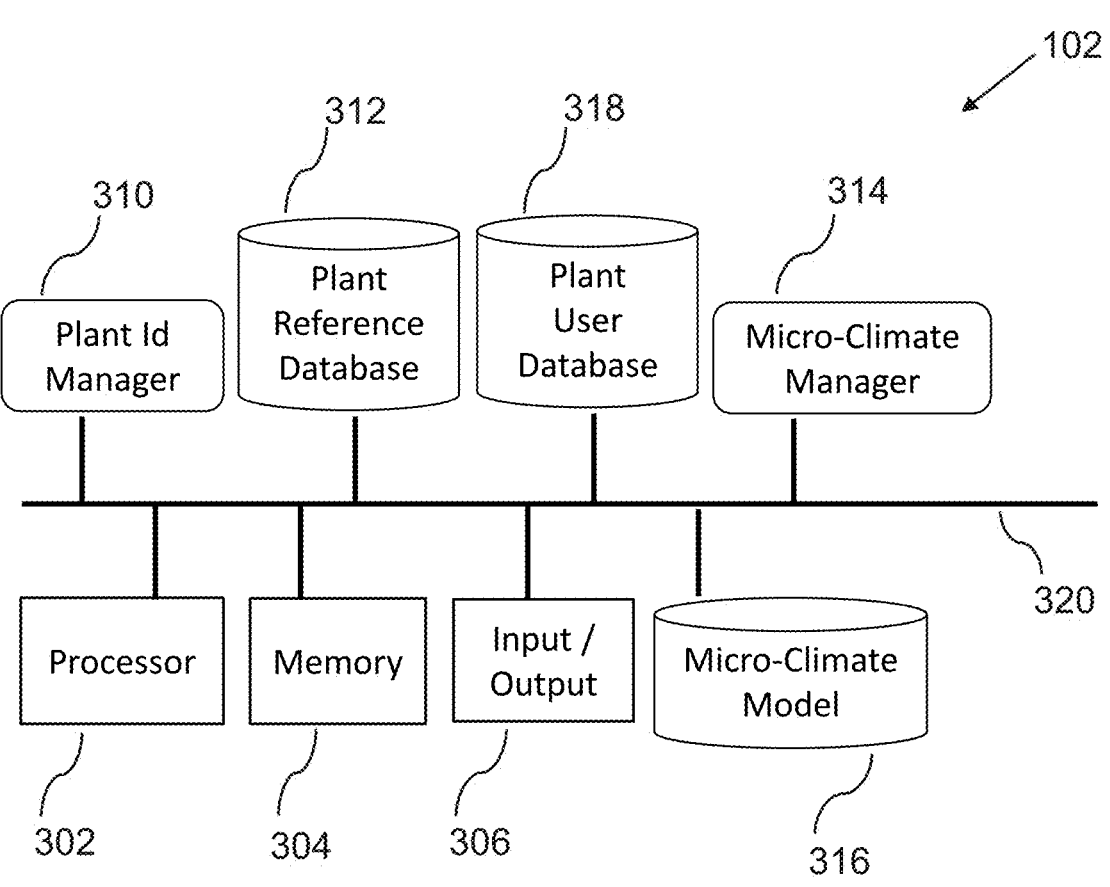
FIG. 3A is a schematic diagram illustrating a plant management server, according to an embodiment of the invention.
Figure 3B:
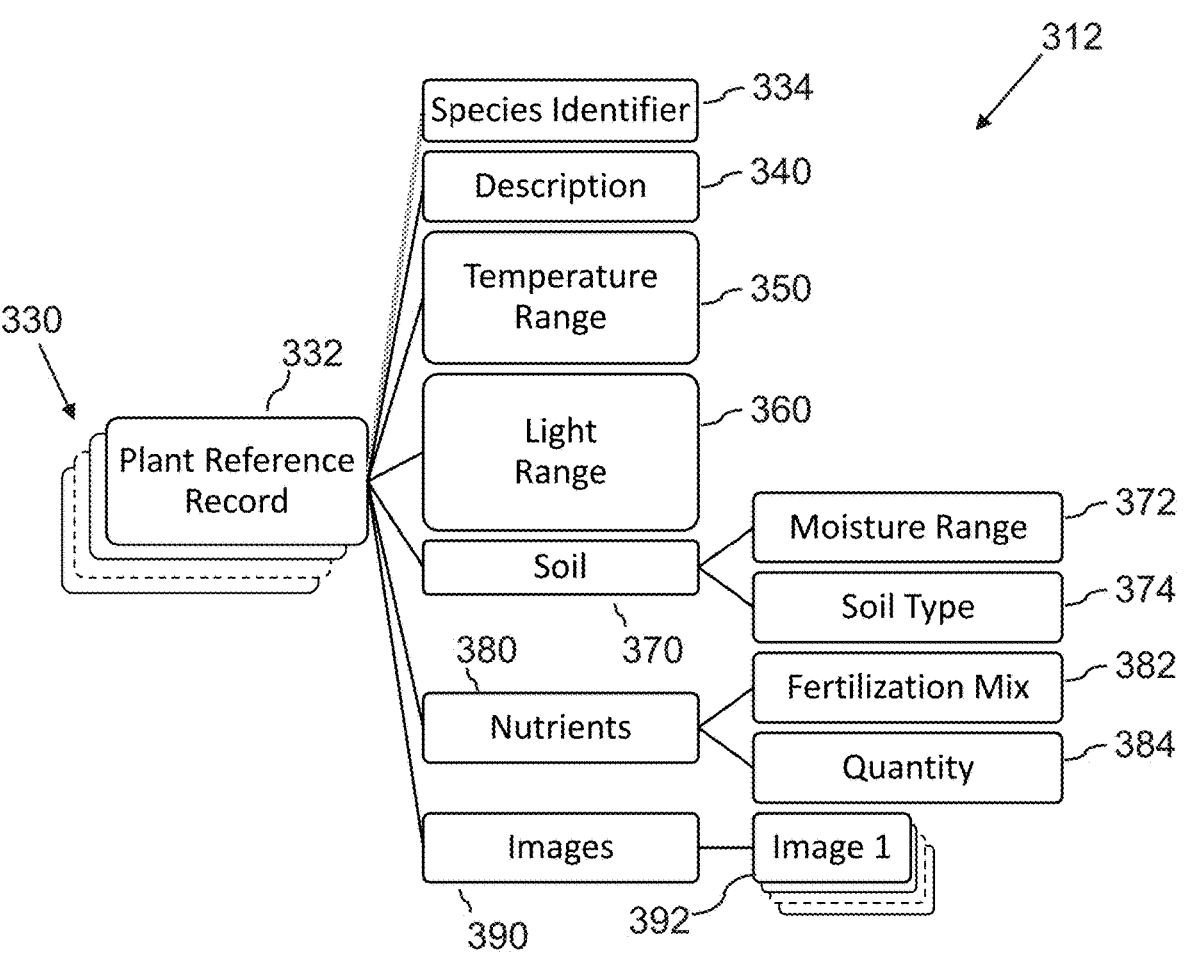
FIG. 3B is a schematic diagram illustrating a plant reference database, according to an embodiment of the invention.
Figure 3C:
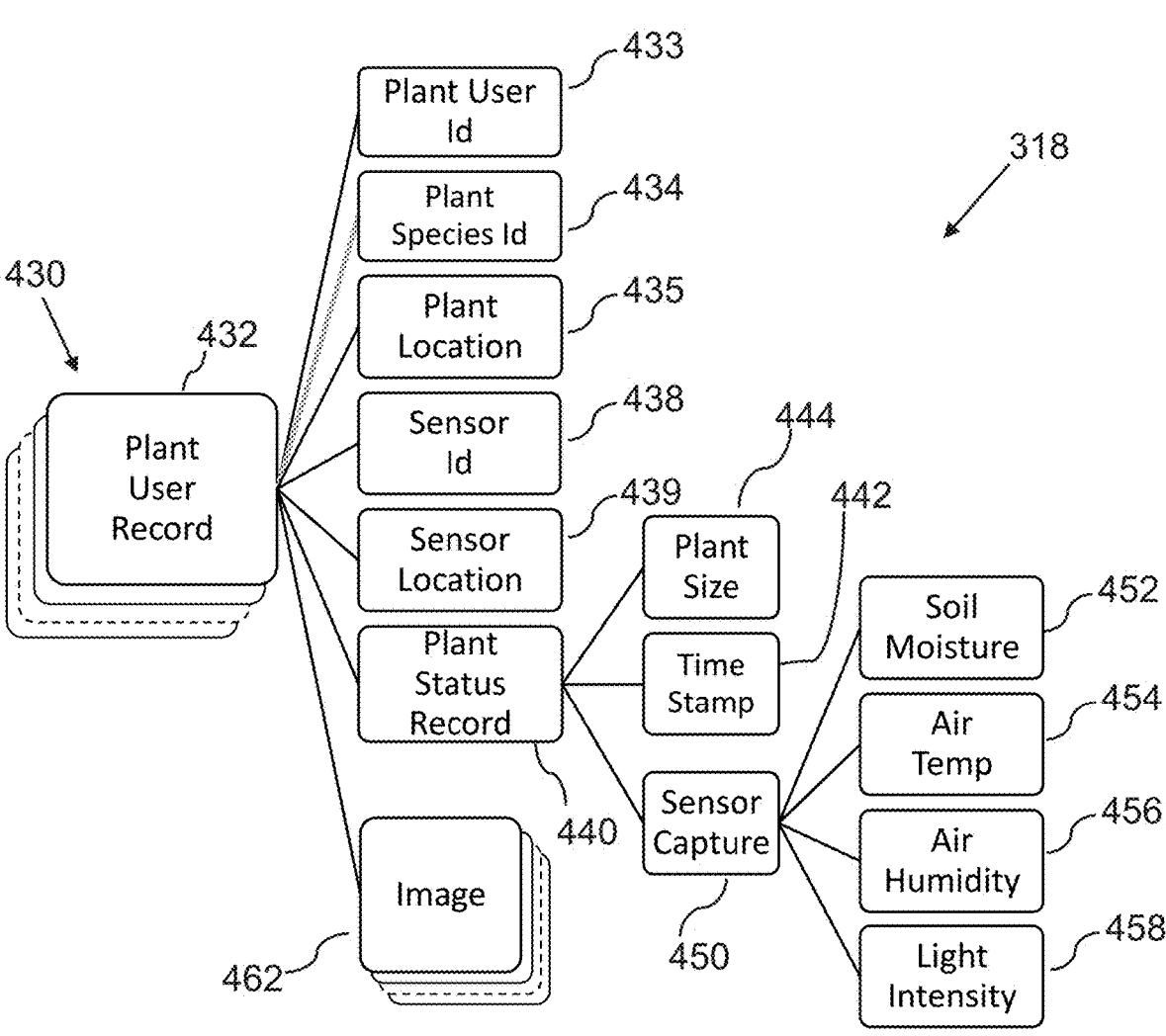
FIG. 3C is a schematic diagram illustrating a plant user database, according to an embodiment of the invention.
Figure 4:
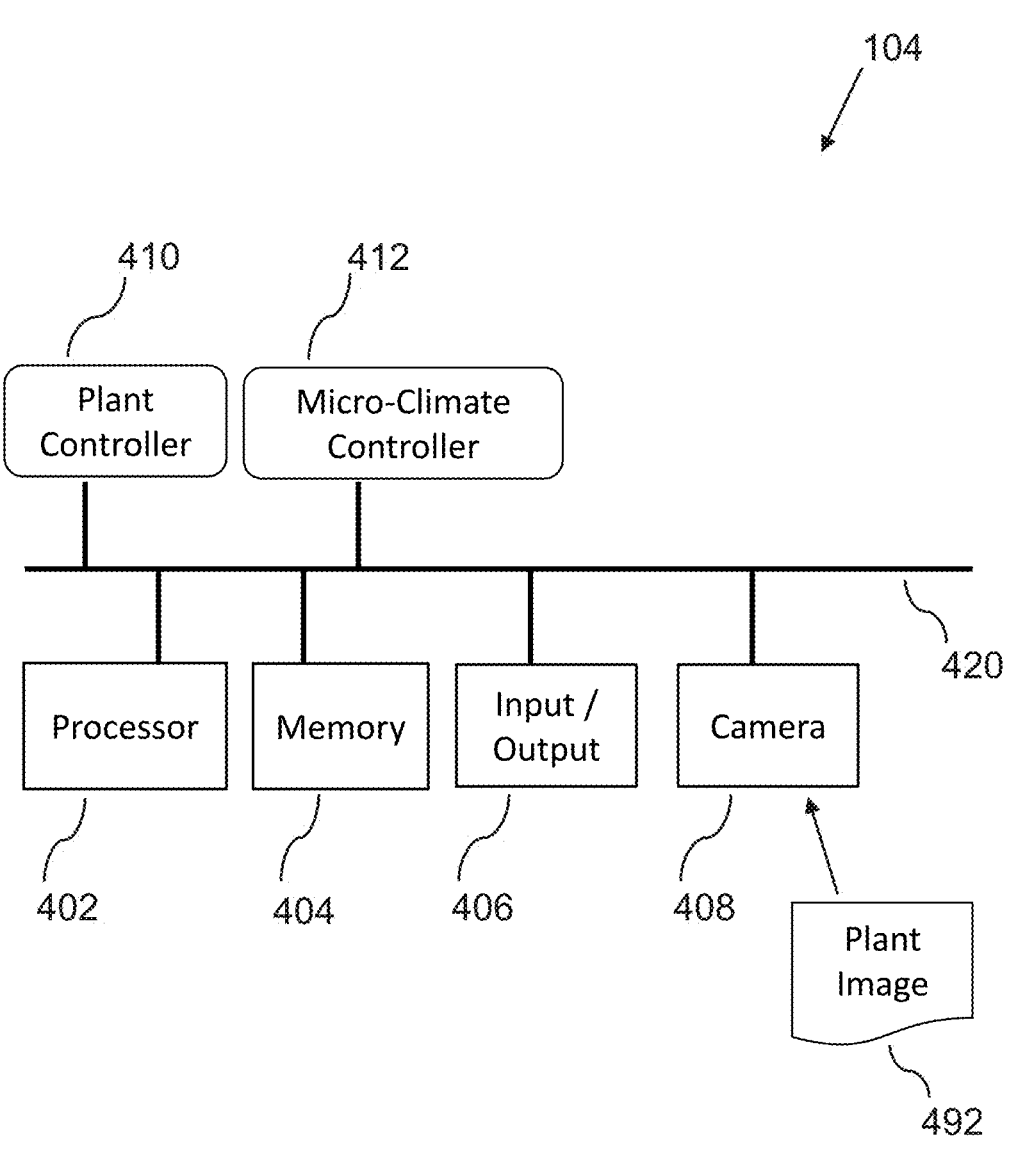
FIG. 4 is a schematic diagram illustrating a plant management control device, according to an embodiment of the invention.
Figure 5A:
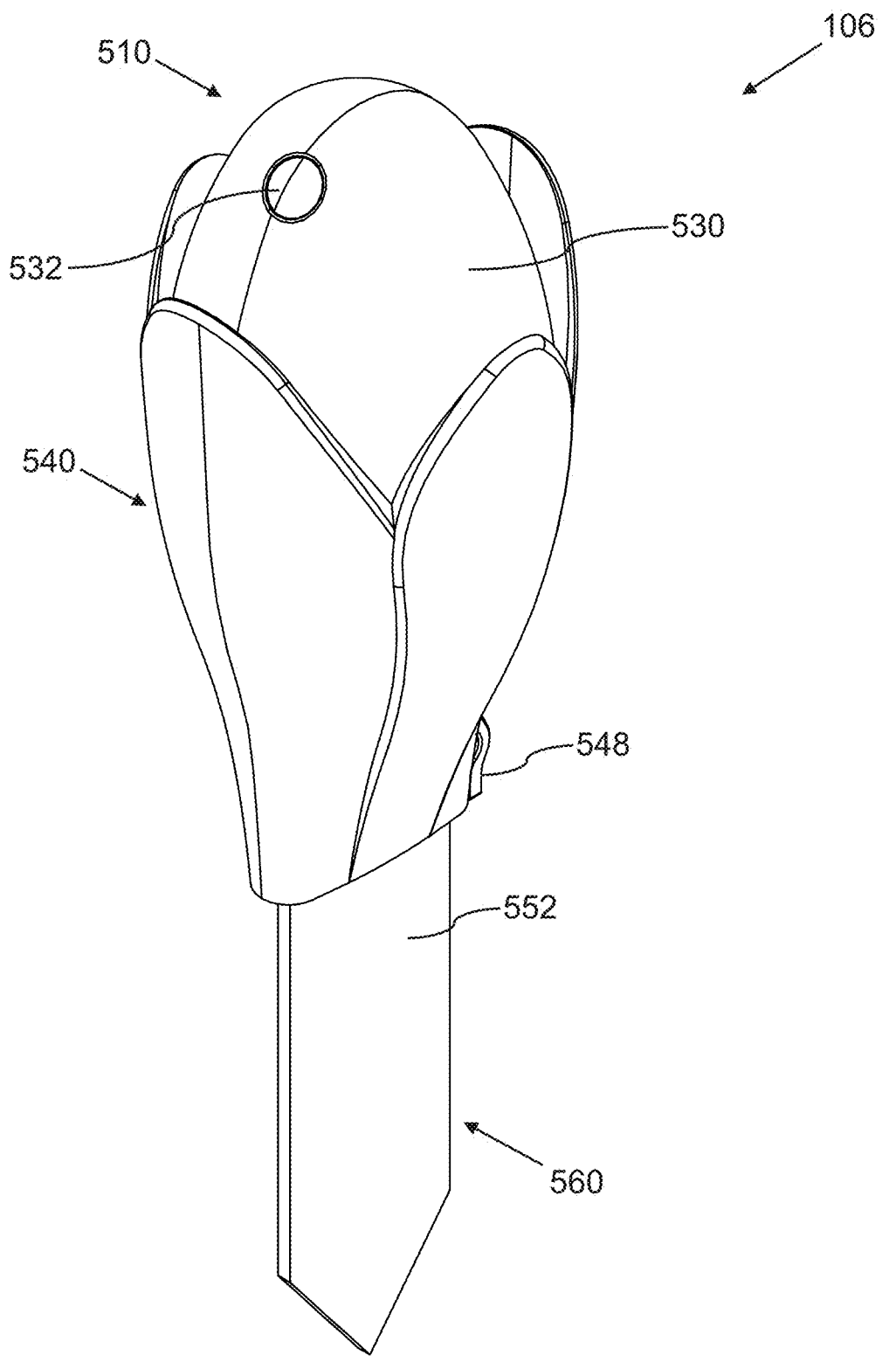
FIG. 5A is a top front left-side perspective view of a plant management sensor device, according to an embodiment of the invention.
Figure 5B:
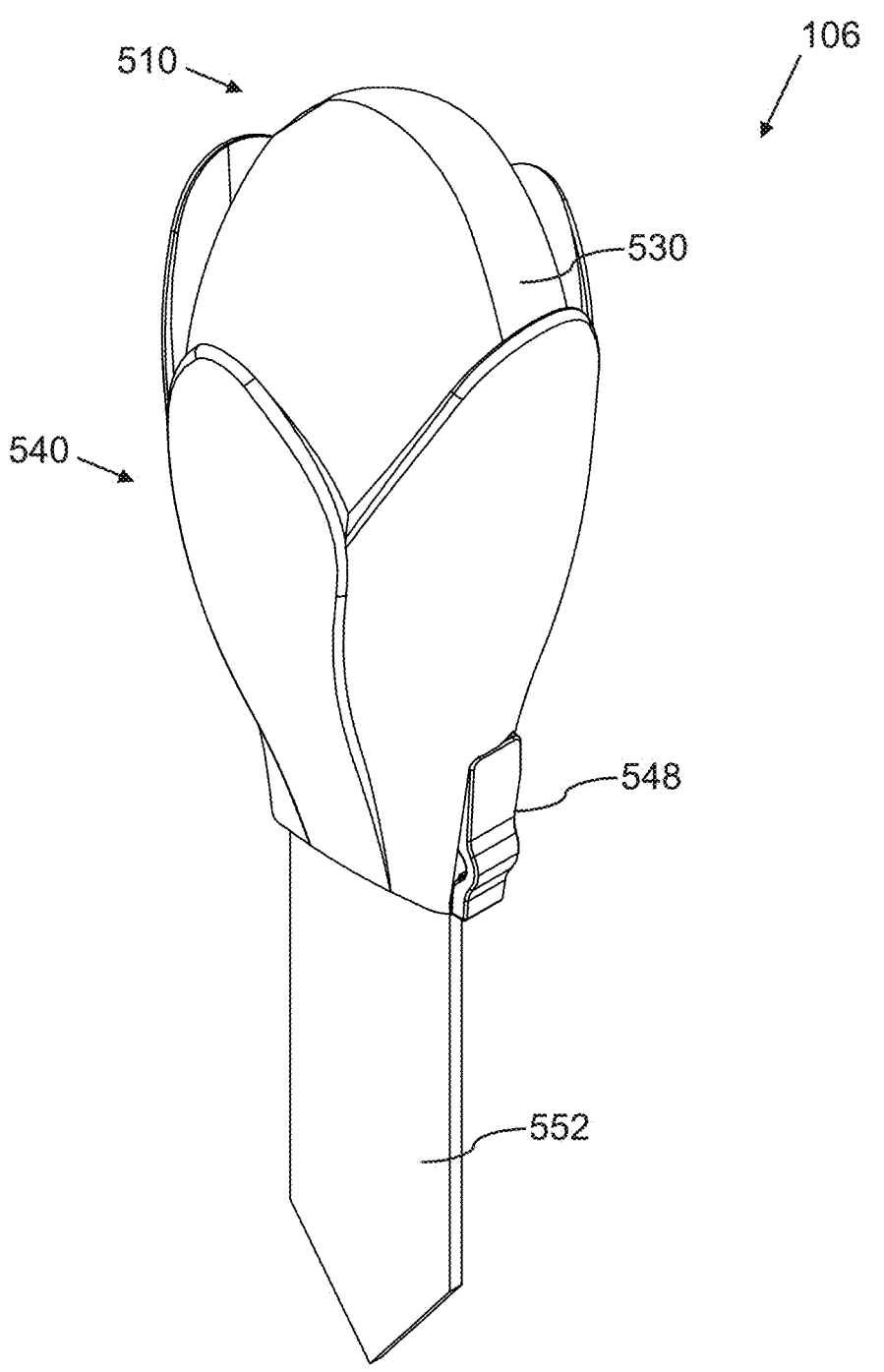
FIG. 5B is a top front right-side perspective view of a plant management sensor device, according to an embodiment of the invention.
Figure 5C:
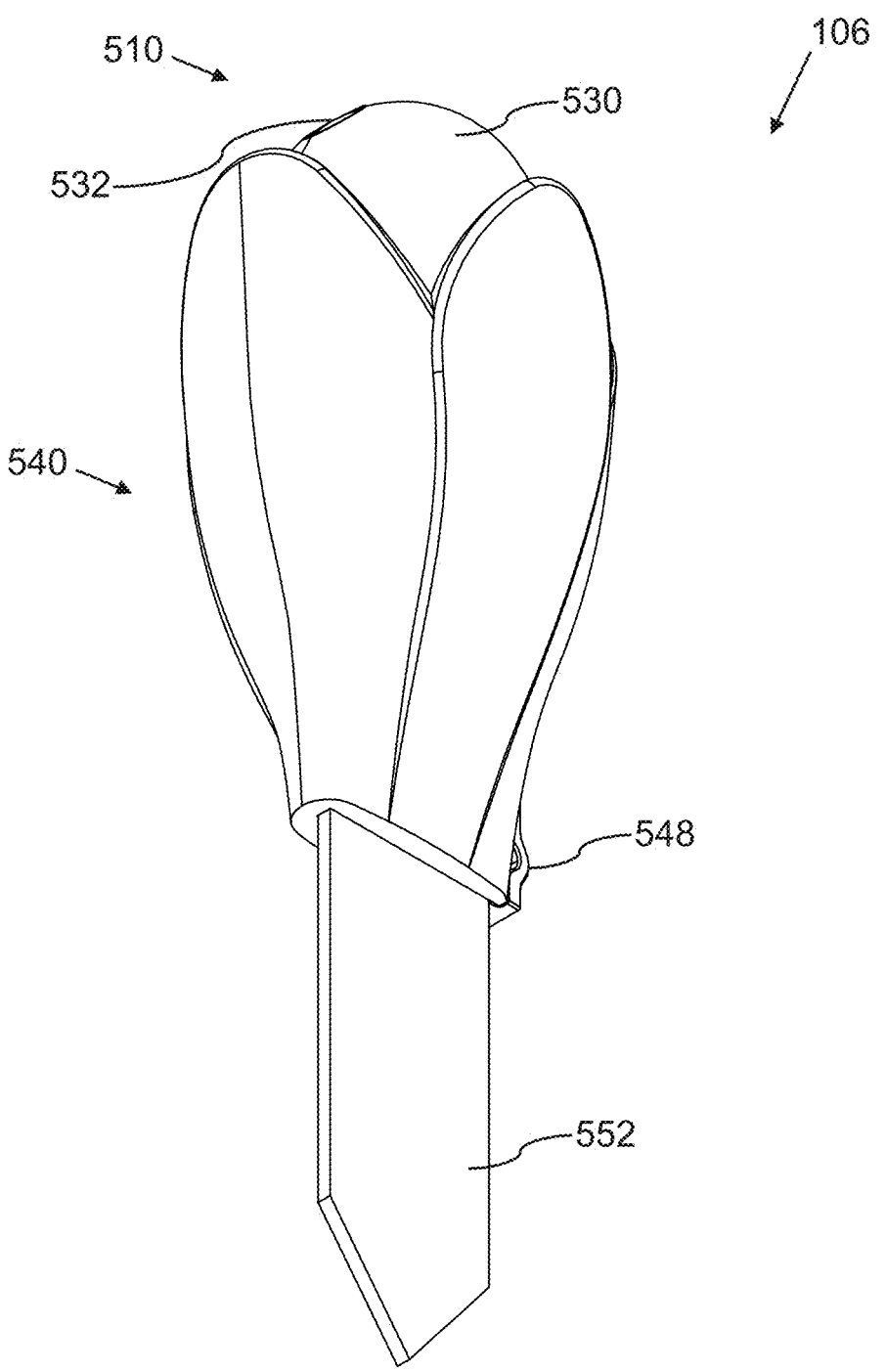
FIG. 5C is a bottom front left-side perspective view of a plant management sensor device, according to an embodiment of the invention.
Figure 5D:
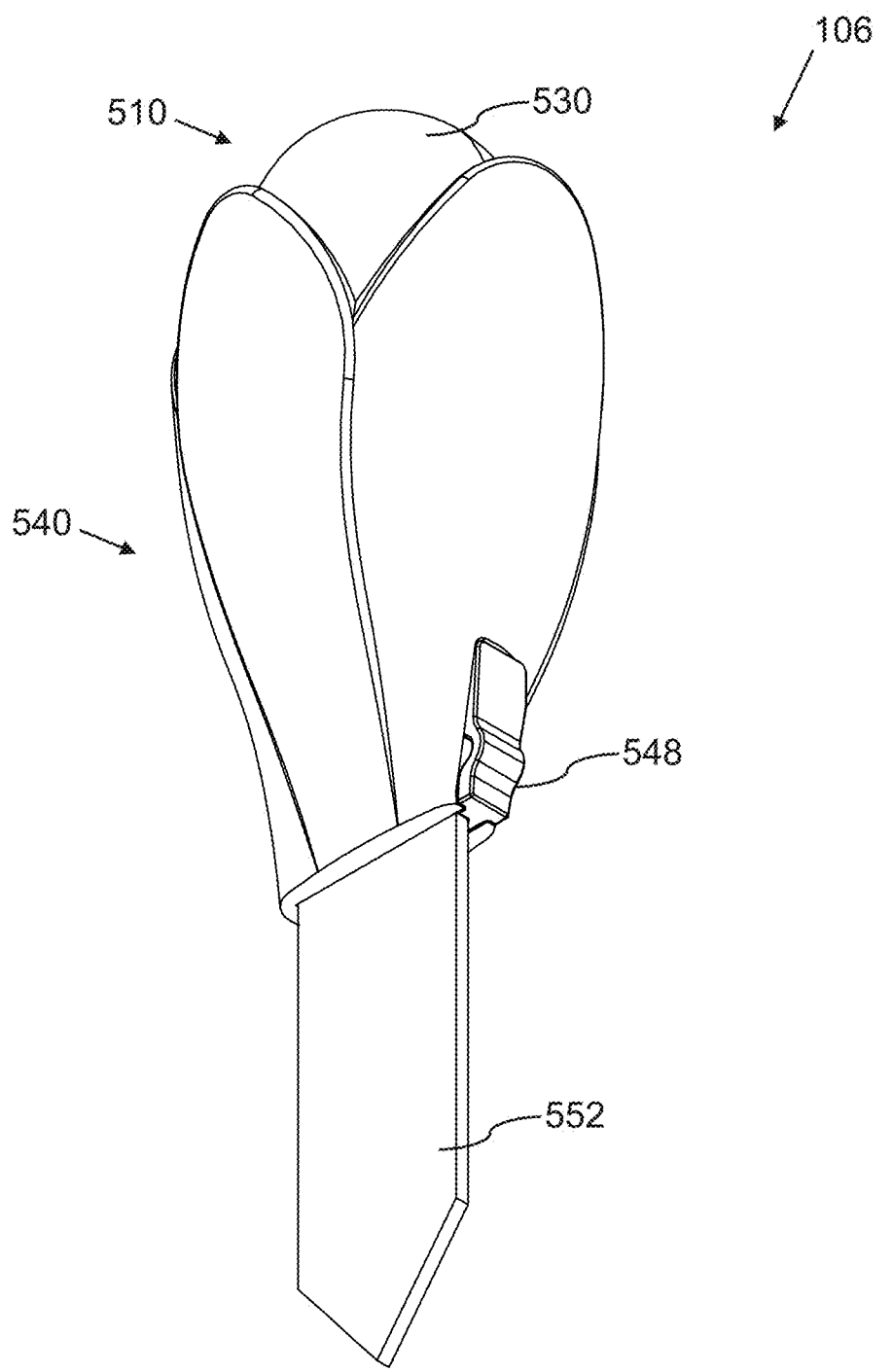
FIG. 5D is a bottom front right-side perspective view of a plant management sensor device, according to an embodiment of the invention.
Figure 5E:
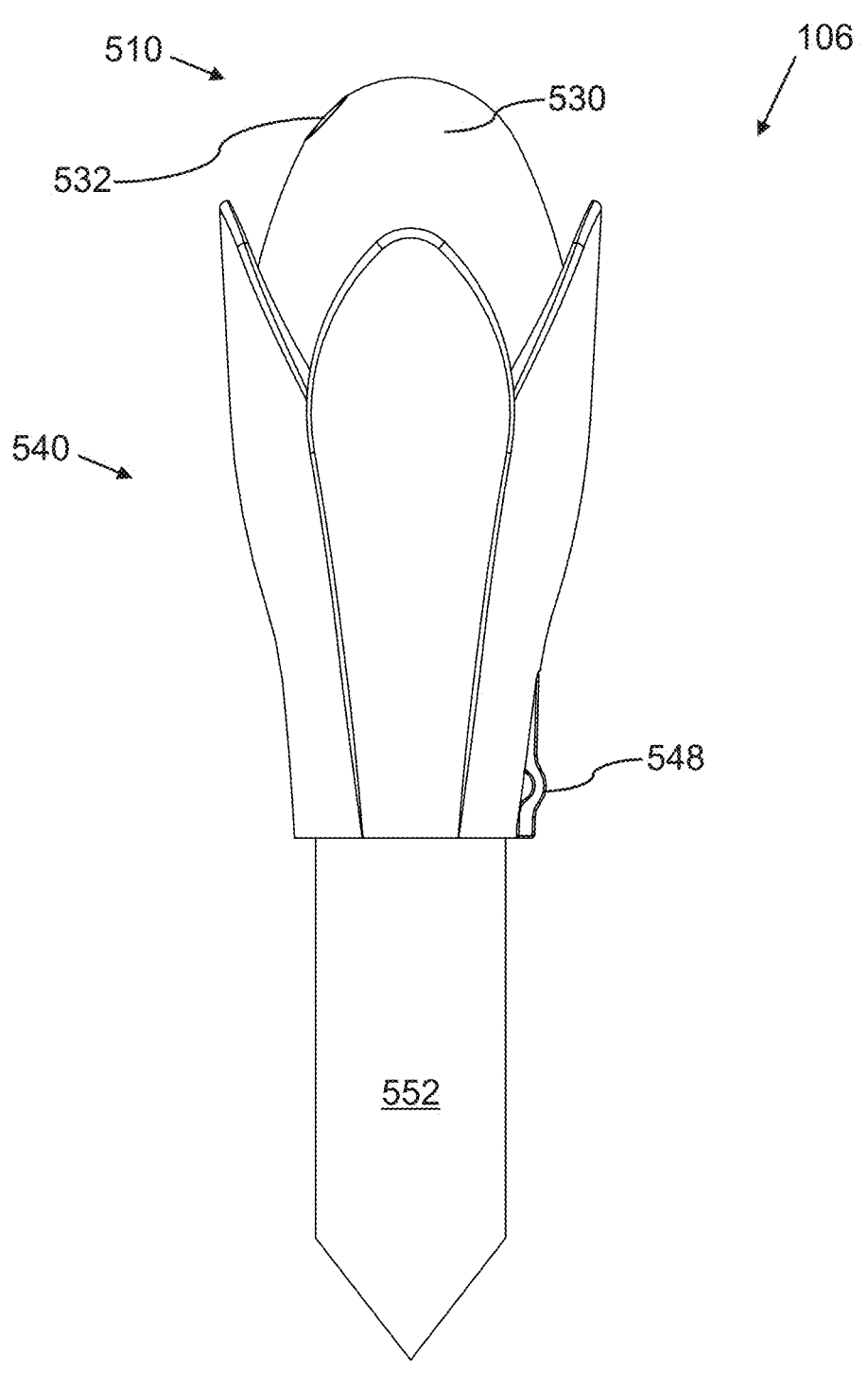
FIG. 5E is a front view of a plant management sensor device, according to an embodiment of the invention.
Figure 5F:
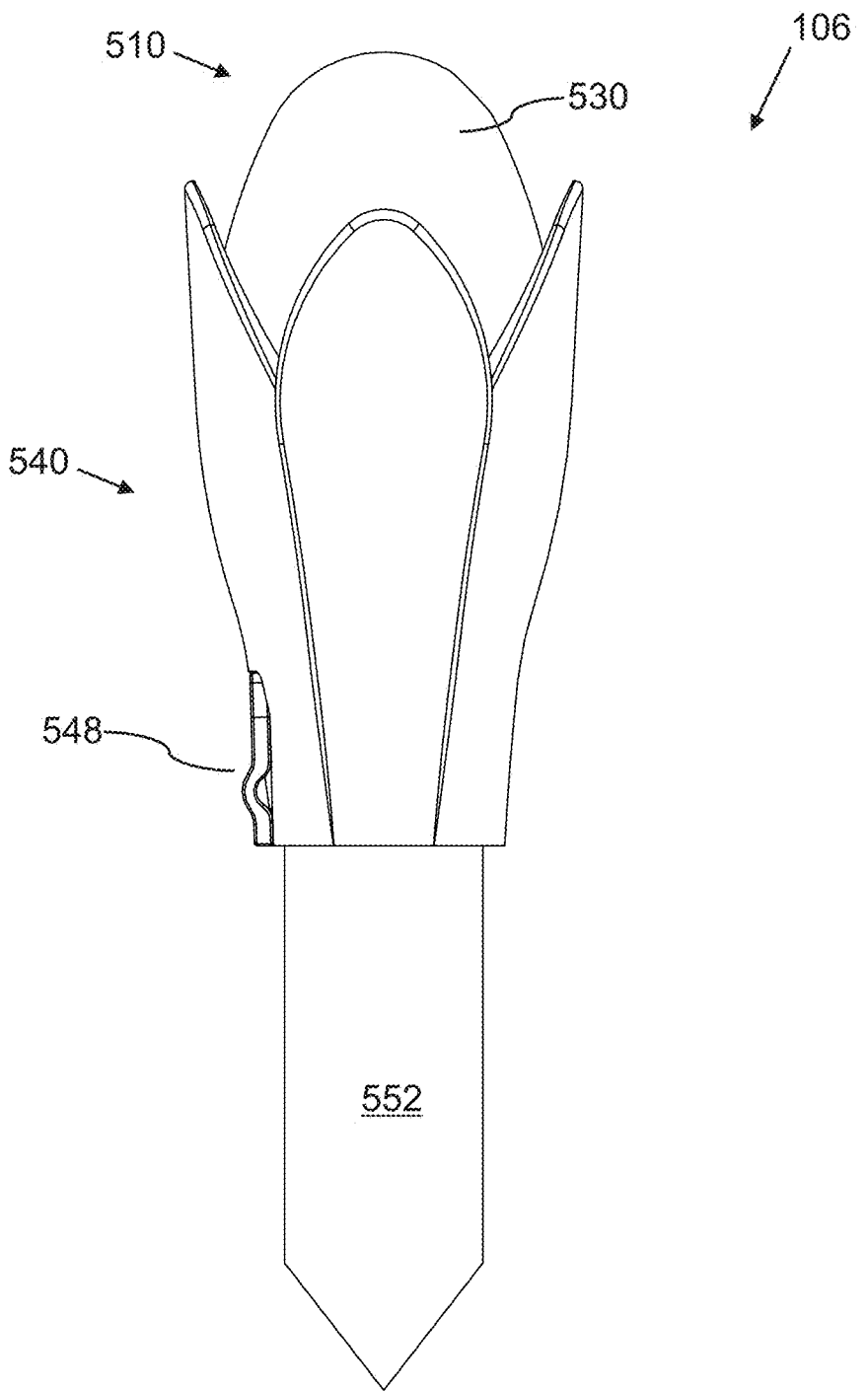
FIG. 5F is a back view of a plant management sensor device, according to an embodiment of the invention.
Figure 5G:
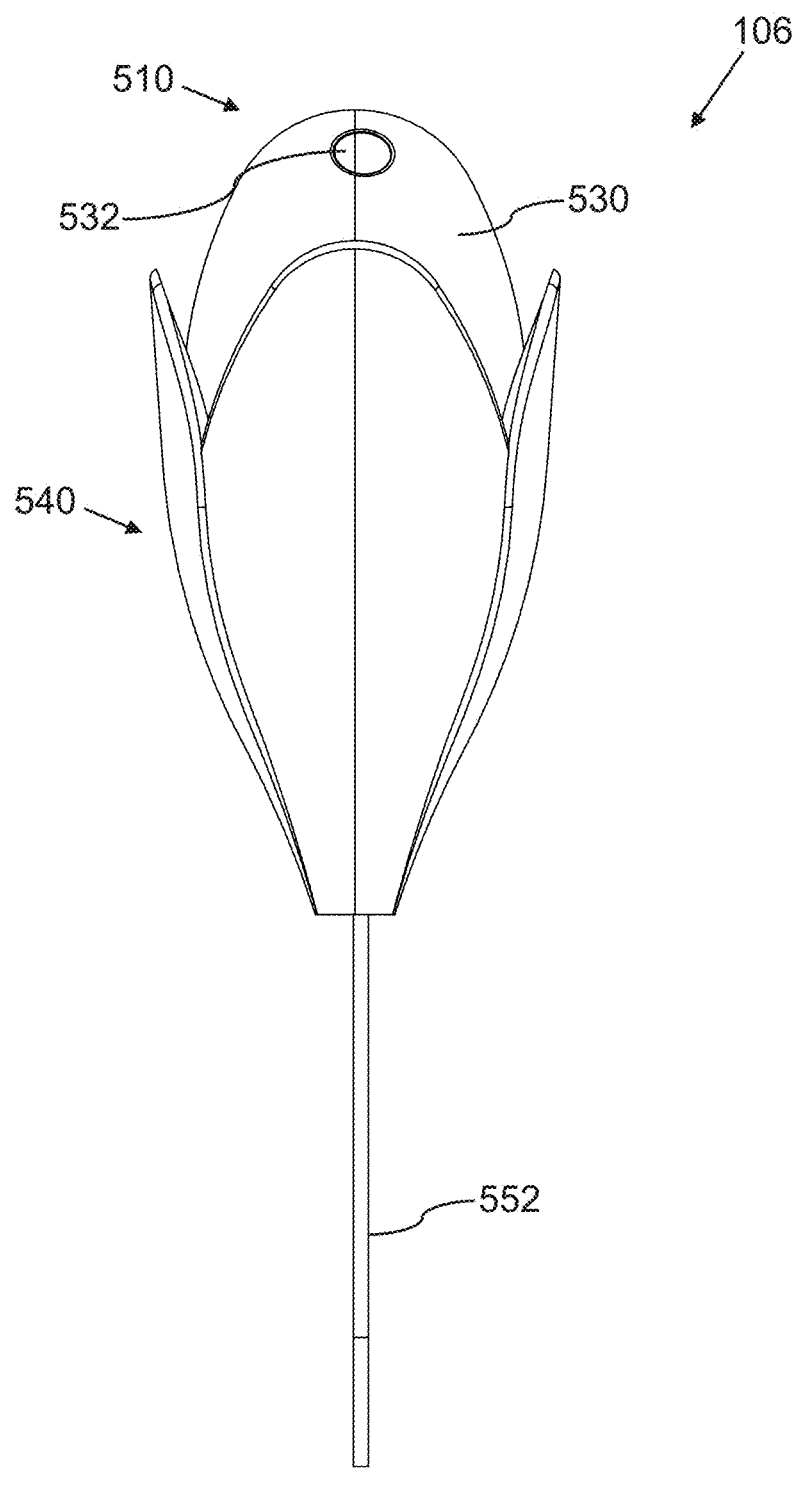
FIG. 5G is a left-side view of a plant management sensor device, according to an embodiment of the invention.
Figure 5H:
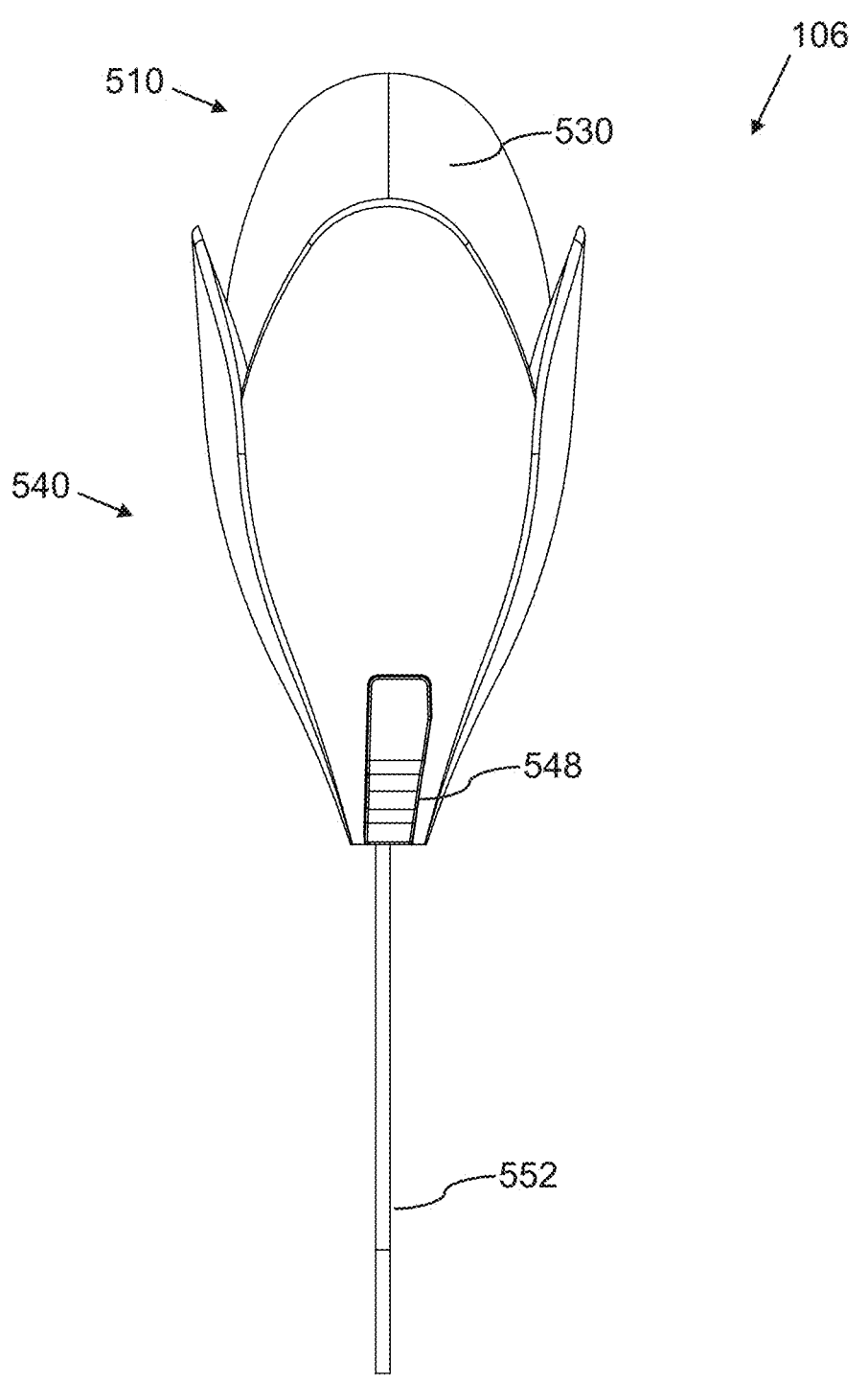
FIG. 5H is a right-side view of a plant management sensor device, according to an embodiment of the invention.
Figure 5I:
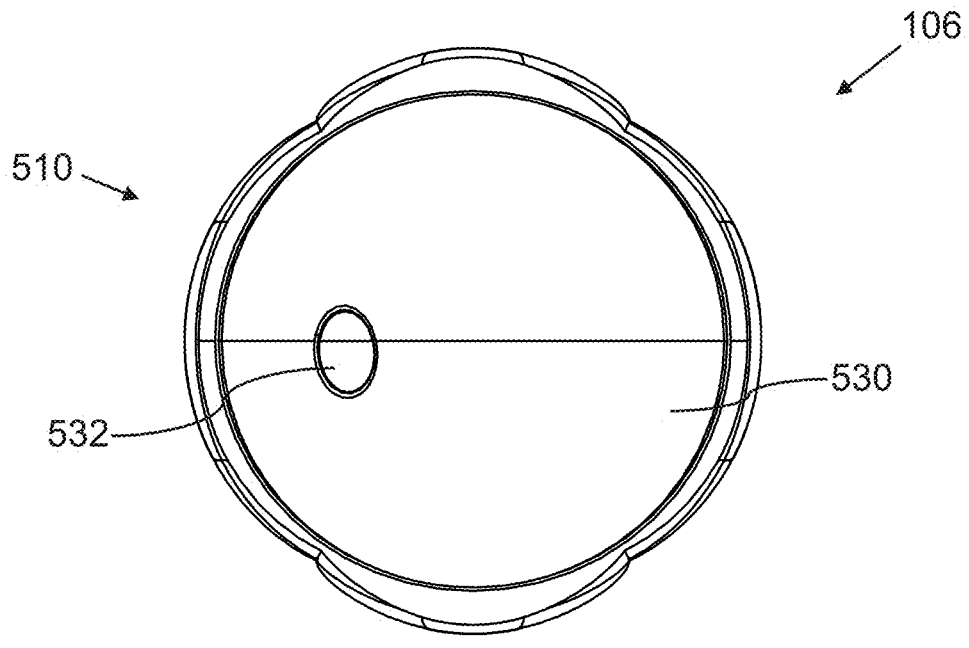
FIG. 5I is a top plan view of a plant management sensor device, according to an embodiment of the invention.
Figure 5J:
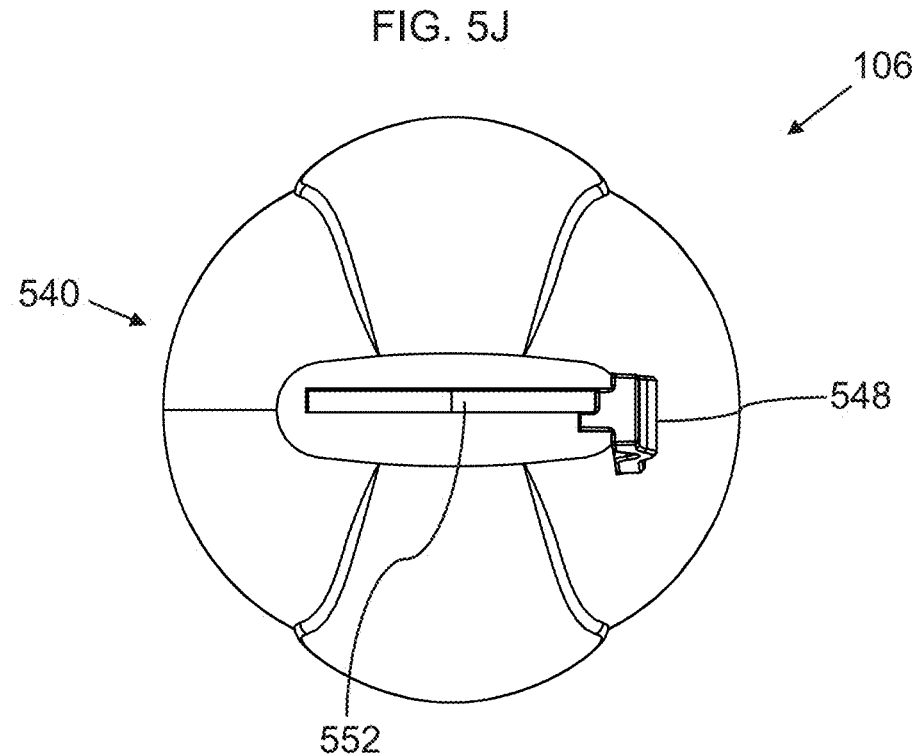
FIG. 5J is a bottom plan view of a plant management sensor device, according to an embodiment of the invention.
Figures 5K, 5L:
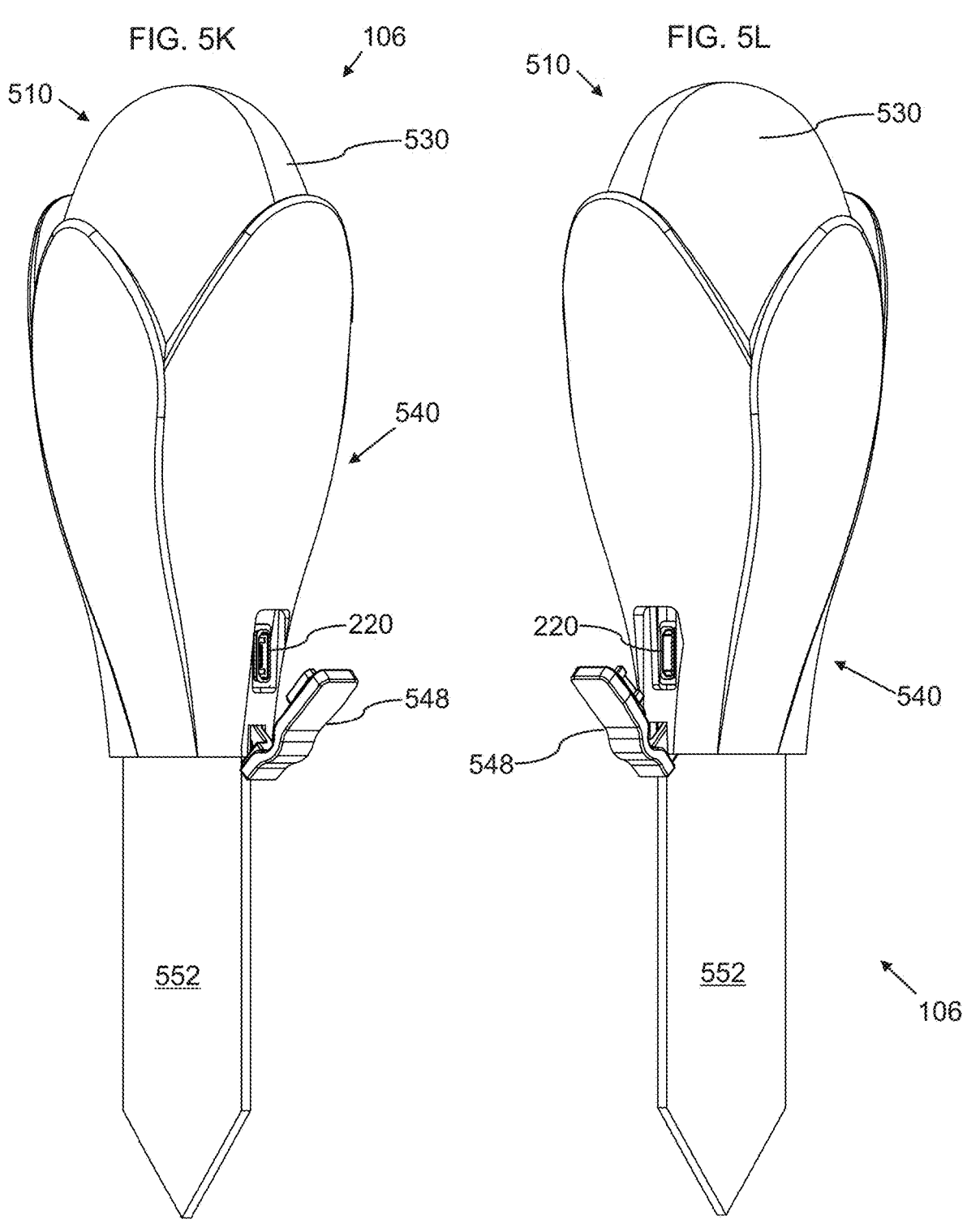
FIG. 5K is a front right-side perspective view of a plant management sensor device, according to an embodiment of the invention.
FIG. 5L is a back right-side perspective view of a plant management sensor device, according to an embodiment of the invention.
Figure 6A:
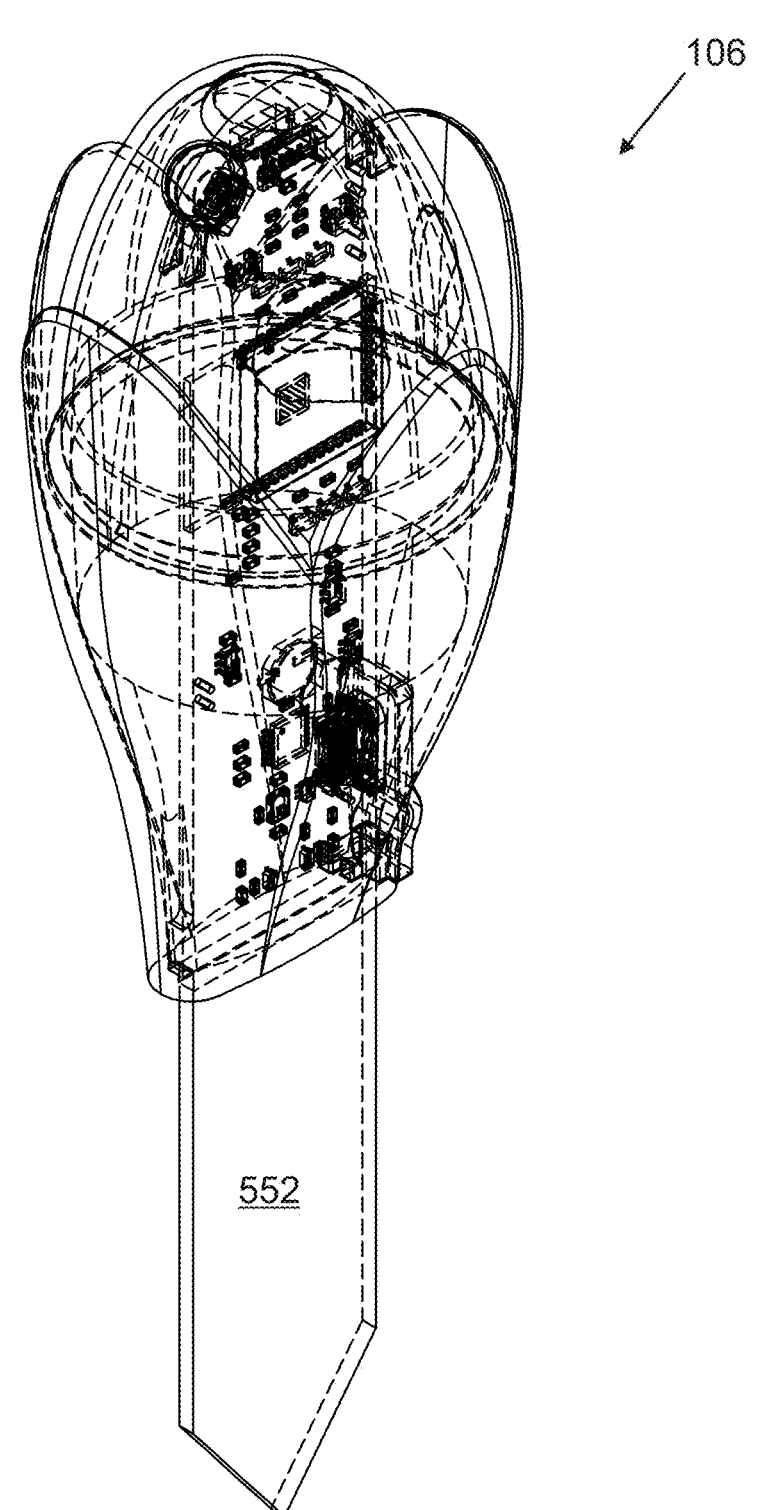
FIG. 6A is a transparent top front left-side perspective view of a plant management sensor device, according to an embodiment of the invention.
Figure 6B:
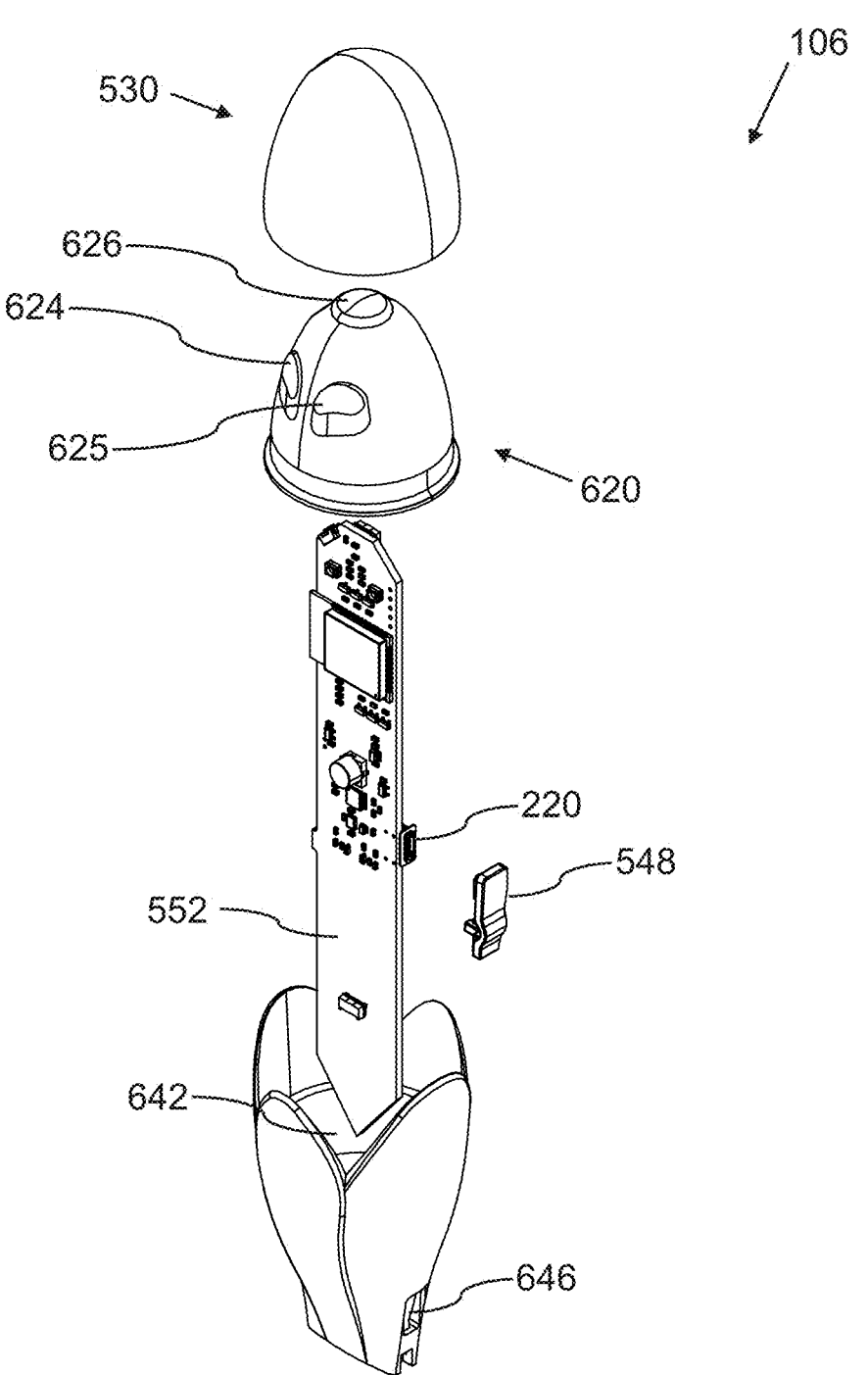
FIG. 6B is an exploded top front right-side perspective view of a plant management sensor device, according to an embodiment of the invention.
Figure 6C:
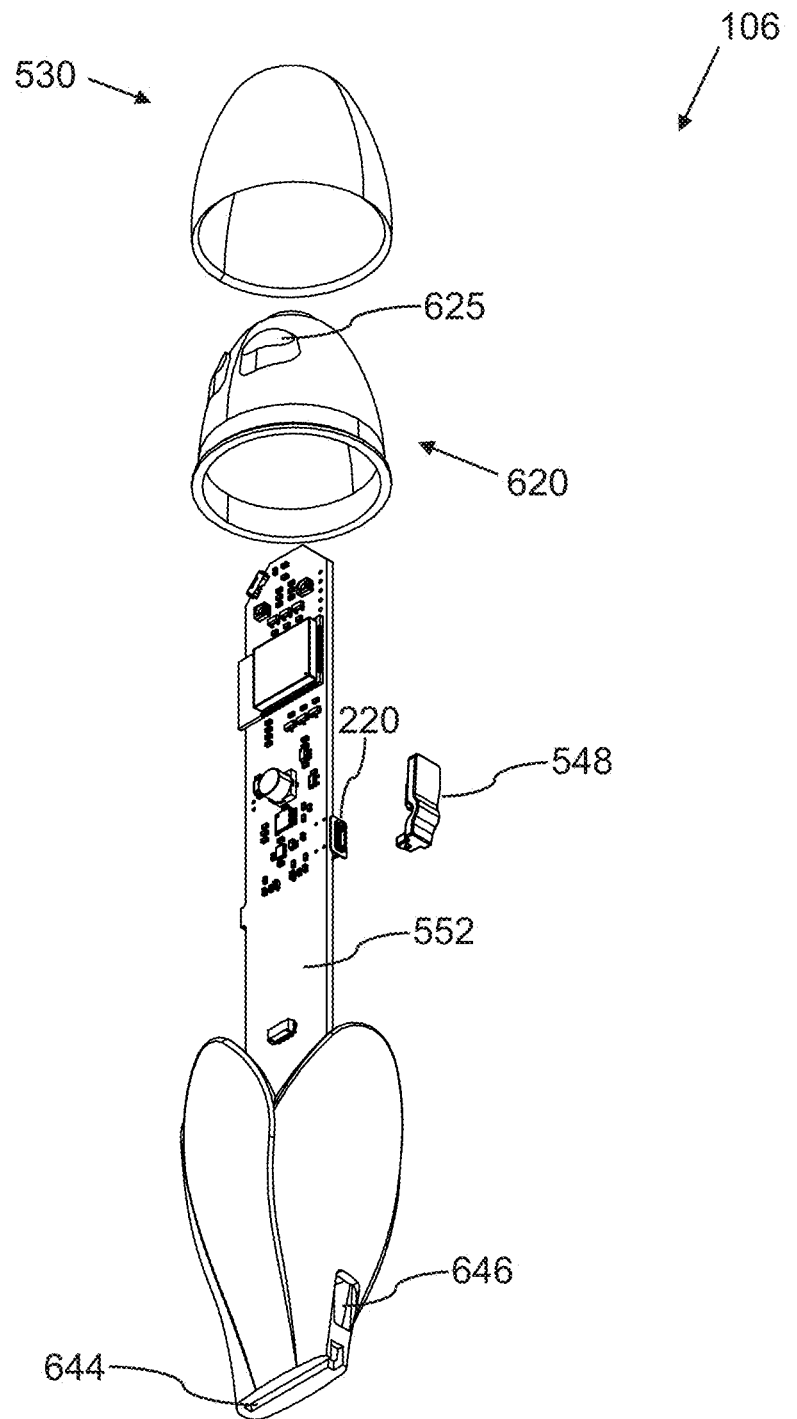
FIG. 6C is an exploded bottom front right-side perspective view of a plant management sensor device, according to an embodiment of the invention.
Figure 6D:
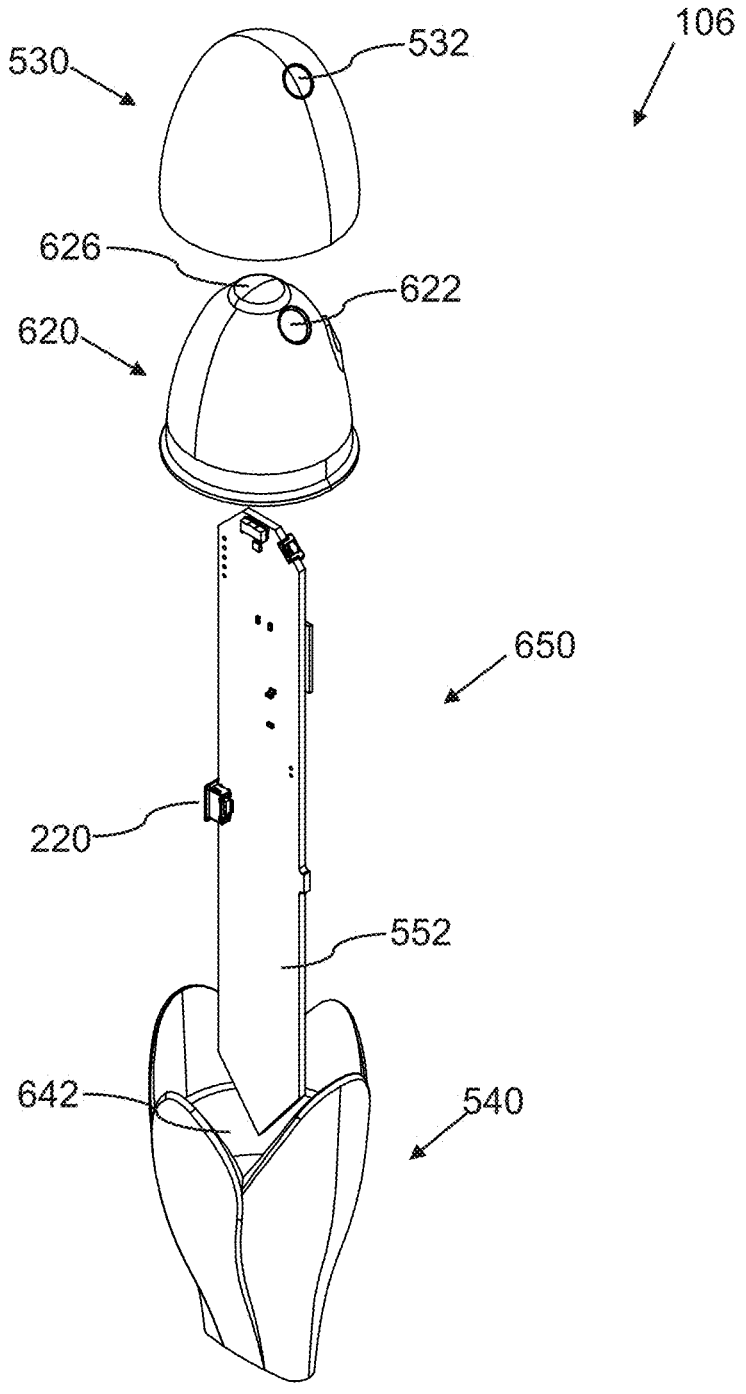
FIG. 6D is an exploded top back left-side perspective view of a plant management sensor device, according to an embodiment of the invention.
Figure 6E:
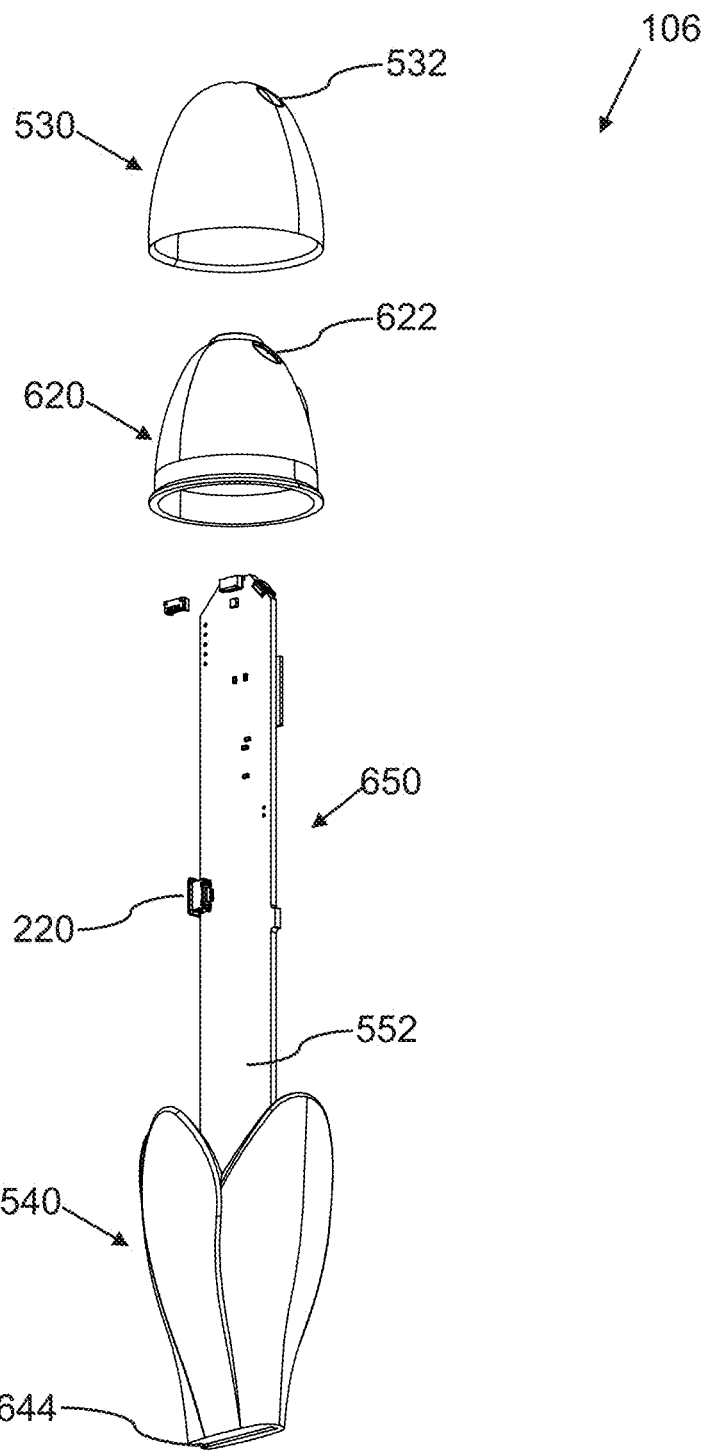
FIG. 6E is an exploded bottom back left-side perspective view of a plant management sensor device, according to an embodiment of the invention.
Figure 7A:
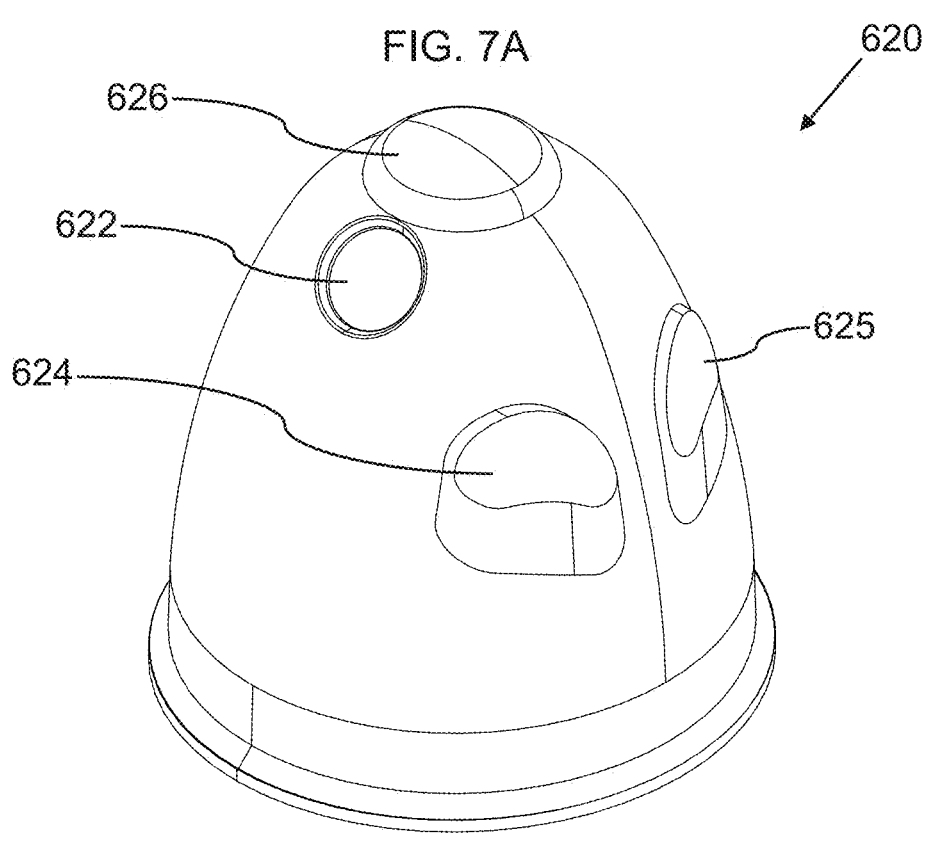
FIG. 7A is a top front left-side perspective view of a main headpiece body.
Figure 7B:
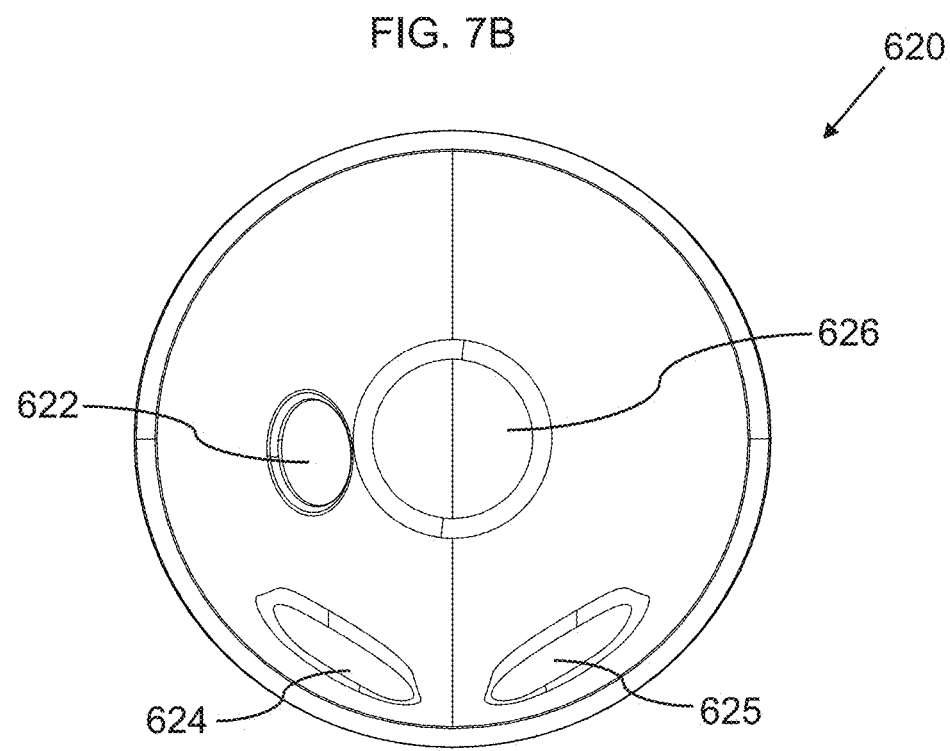
FIG. 7B is a top view of a main headpiece body.
Figure 8A:
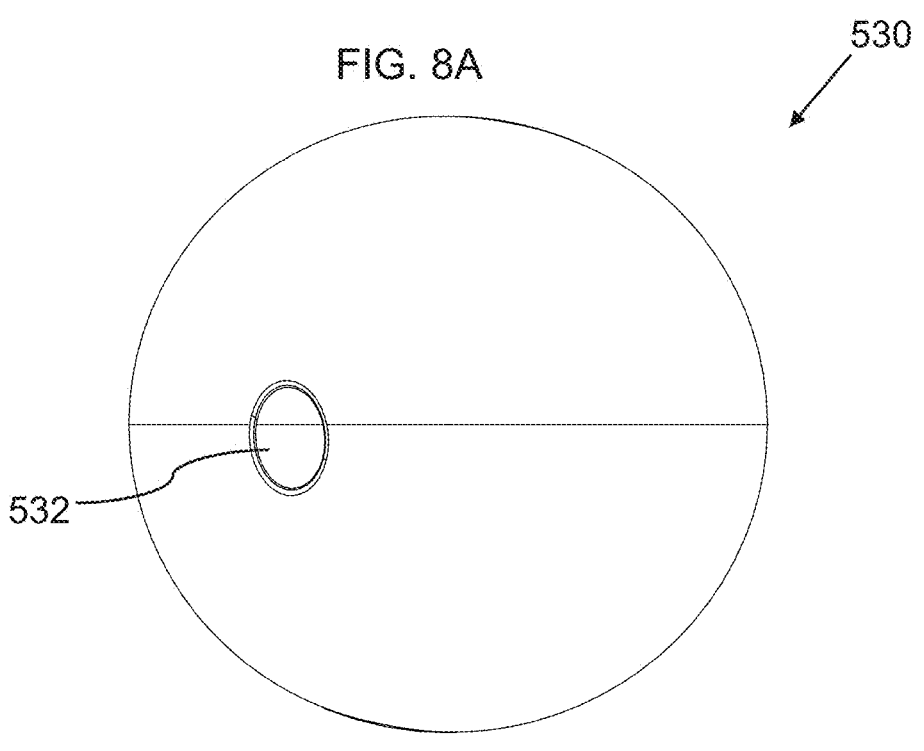
FIG. 8A is a top view of a headpiece overmold.
Figure 8B:
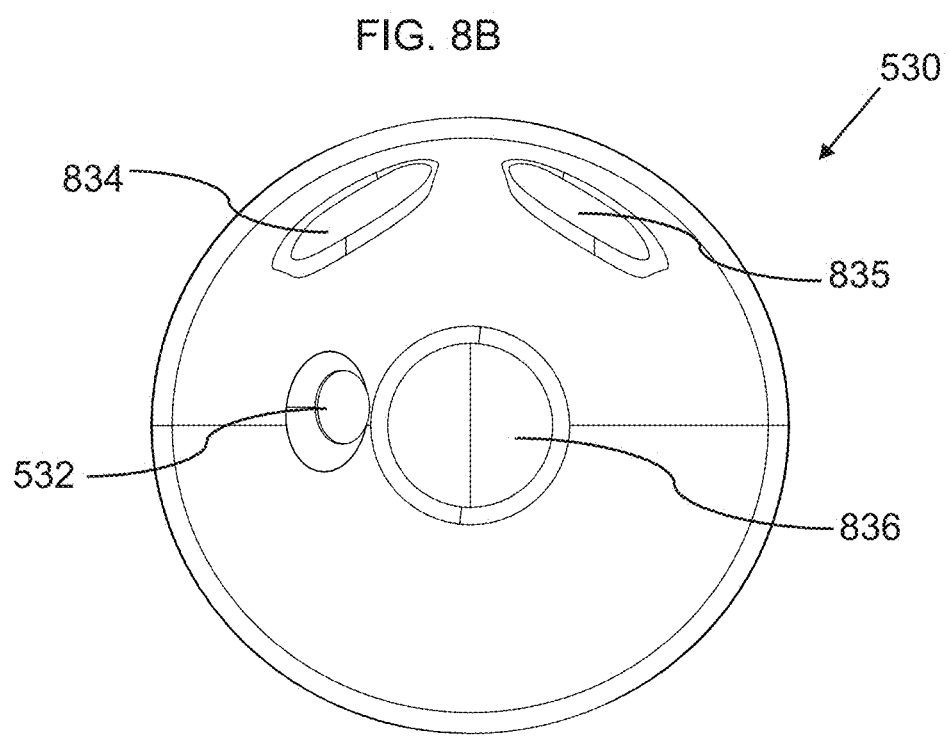
FIG. 8B is a bottom view of a headpiece overmold.

In a related embodiment, as shown in FIG. 3B, the plant management server 102 can include:

a) A processor 302;

b) A non-transitory memory 304;

c) An input/output component 306;

d) A plant id manager 310, which can be configured to identify a plant species, based on a plant actual image, which is captured by a camera 408 of the plant management control device 104;

e) A plant reference database 312, which comprises a library of plant reference information, wherein the plant reference database 312 can include:

i. a plurality of plant user records;

wherein the plant id manager 310 can be configured to identify the plant actual image to match a plant reference images by a search in the plant reference database 312; and f) A plant user database 318, which comprises a library of plant user information related to plants 182, 184 in the garden bed 180 of the user 116, wherein the plant user database 318 can include:

ii. a plurality of plant user records;

g) A micro-climate manager 314, which is configured to capture, store, and process local climate information from the at least one plant management sensor device 106; all connected via h) A data bus 320;

In a related embodiment, as shown in FIG. 3B, the plant reference database 312 can include a plurality 330 of plant reference records 332, each including:

a) A plant species identifier 334;

b) A plant description 340, which can for example include:

i. General description;

ii. Binomial name;

iii. Scientific classification: Family, genus, species, etc.; and iv. Habitat and Geographical distribution;

c) A plant temperature range 350;

d) A plant light exposure range 360;

e) A plant soil descriptor 370, which can include:

i. a plant soil moisture range 372; and ii. a plant soil type 374;

f) A plant nutrient descriptor 380, which can include:

i. a plant fertilization mix 382; and ii. a plant fertilization quantity 384; and g) Images 390, which can include:

i. at least one plant reference image 392.

In a related embodiment, the plant management control device 104, can include:

a) A processor 402;

b) A non-transitory memory 404;

c) An input/output 406;

d) A camera 408, such that a plant actual image of a physical plant 182, 184 can be captured by the camera 408;

e) A plant controller 410, which is configured to view and process plant information, received from the plant reference database 312, in communication via the plant management server 102; and f) A micro-climate controller 412, which is configured to view and process climate information, received from:

i. the plant reference database 312, in communication via the plant management server 102; and/or ii. the at least one plant management sensor device 106, either in direct communication between the plant management control device 104 and the at least one plant management sensor device 106 or via the plant management server 102 (as shown in FIG. 1); all connected via g) A data bus 420.

In a related embodiment, the plant management sensor device 106, can further include:

a) a headpiece assembly 510, which can be a solid body which can be used to seal the top portion of a floral body interior 642, and which can include:

i. a main headpiece body 620, which can be a paraboloid shape, and which can be configured to attach to a floral body 540, and which can include:

1. a button aperture 622, which can be an aperture which can be configured to house a headpiece button 532;

2. a first protrusion 624, which can be a protrusion from the main headpiece body 620, and which can be configured to interface with a first overmold cavity 834;

3. a second protrusion 625, which can be a protrusion from the main headpiece body 620, and which can be configured to interface with a second overmold cavity 835; and 4. a third protrusion 626, which can be a protrusion from the main headpiece body 620, and which can be configured to interface with a third overmold cavity 836; and ii. a headpiece overmold 530, which can be a paraboloid shaped solid body, which can be configured to sit flush with the main headpiece body 620, which can also include:

1. a headpiece button 532, which can be an analog or digital switch which can be used to control an electronic function of the plant management sensor device, and which can be configured to protrude through a button aperture 622;

2. a first overmold cavity 834, which can be a cavity in the headpiece overmold 530, which can be constructed to house a first protrusion 624, of a main headpiece body 620;

3. a second overmold cavity 835, which can be a cavity in the headpiece overmold 530, which can be constructed to house a second protrusion 625, of a main headpiece body 620;

4. a third overmold cavity 836, which can be a cavity in the headpiece overmold 530, which can be constructed to house a third protrusion 626, of a main headpiece body 620;

such that the headpiece overmold 530, can be attached to and be flush with the main headpiece body 620; and b) a floral body 540, which can be a solid body which can be configured to visually resemble a plant, and which can include:

i. a floral body interior 642, which can be a vacant region inside the floral body 540, which can be configured to house a PCB assembly 650;

ii. a PCB aperture 644, which can be an aperture which can be configured to allow the insertion of a PCB assembly 650, into the aperture;

iii. a USB aperture 646, which can be an aperture which can be configured to allow access to a USB port through the aperture;

iv. a USB cap 548, which can be cover member, which can be configured to allow or disallow access to an electronics assembly 954, which can be housed in the floral body cavity 642; and c) a PCB assembly 650, which can include:

i. a PCB main body 552, which can be a single layer of PCB or a plurality thereof, which can contain traces and which can be configured to be insertable into a PCB aperture 644;

ii. an electronics assembly 954, which can be a circuit or plurality thereof, and which can include a USB port;

wherein the headpiece assembly 510, can be connected to the floral body 540, and the PCB assembly 650, can be an attached to the floral body 540, such that the PCB assembly 650, can protrude from the bottom portion of the floral body 540.

In a related embodiment, a copper probe node 209, of an electronics assembly 954, can be embedded into a layer of a PCB main body 552, of a PCB assembly 650.

In a related embodiment, the PCB main body 552, can be configured to include a stake-like geometry, which can aid in the installation of the plant management sensor device 106.

In various embodiments, the plant management system 100 can automatically, wirelessly and/or by wired connections, relay sensor data to a user 116, to help them save their plants, and aggregate the sensor data with at least two layers of machine-learning, wherein the machine learning can include:

a) image classification to identify plant species and adjust sensor data thresholds accordingly; and b) analysis of location-based data where we aggregated anonymized user data to adjust micro-climate data for the user's plant and also adjust thresholds accordingly.

In a related embodiment, the plant management sensor device 106, can include a Wi-Fi/Bluetooth microcontroller that communicates with a light sensor and a temperature/relative humidity sensor.

Figures 9A, 9B, 9C:
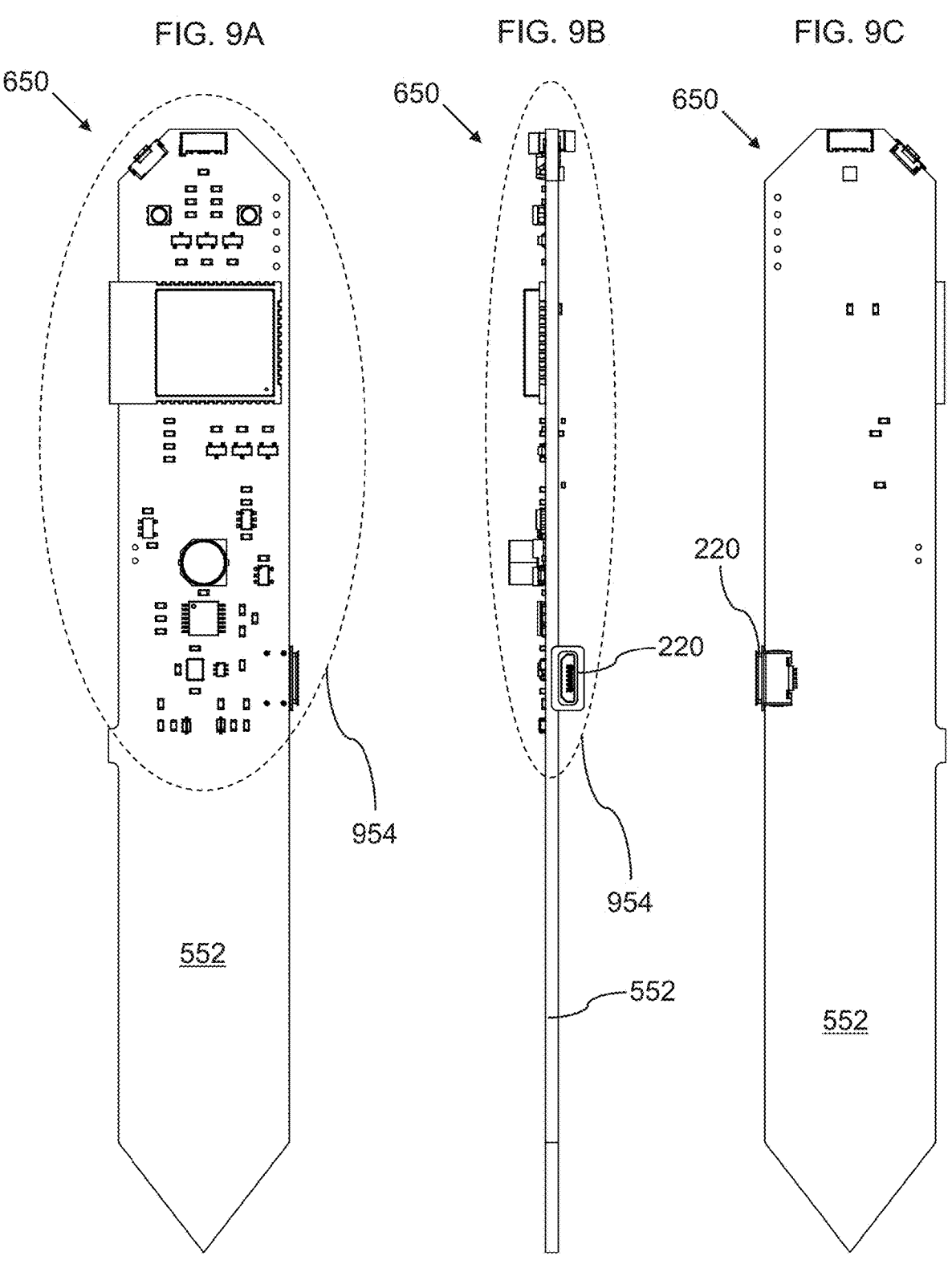
FIG. 9A is a front view of a PCB assembly, according to an embodiment of the invention.
FIG. 9B is a right-side view of a PCB assembly, according to an embodiment of the invention.
FIG. 9C is a back view of a PCB assembly, according to an embodiment of the invention.
Figures 9D, 9E:
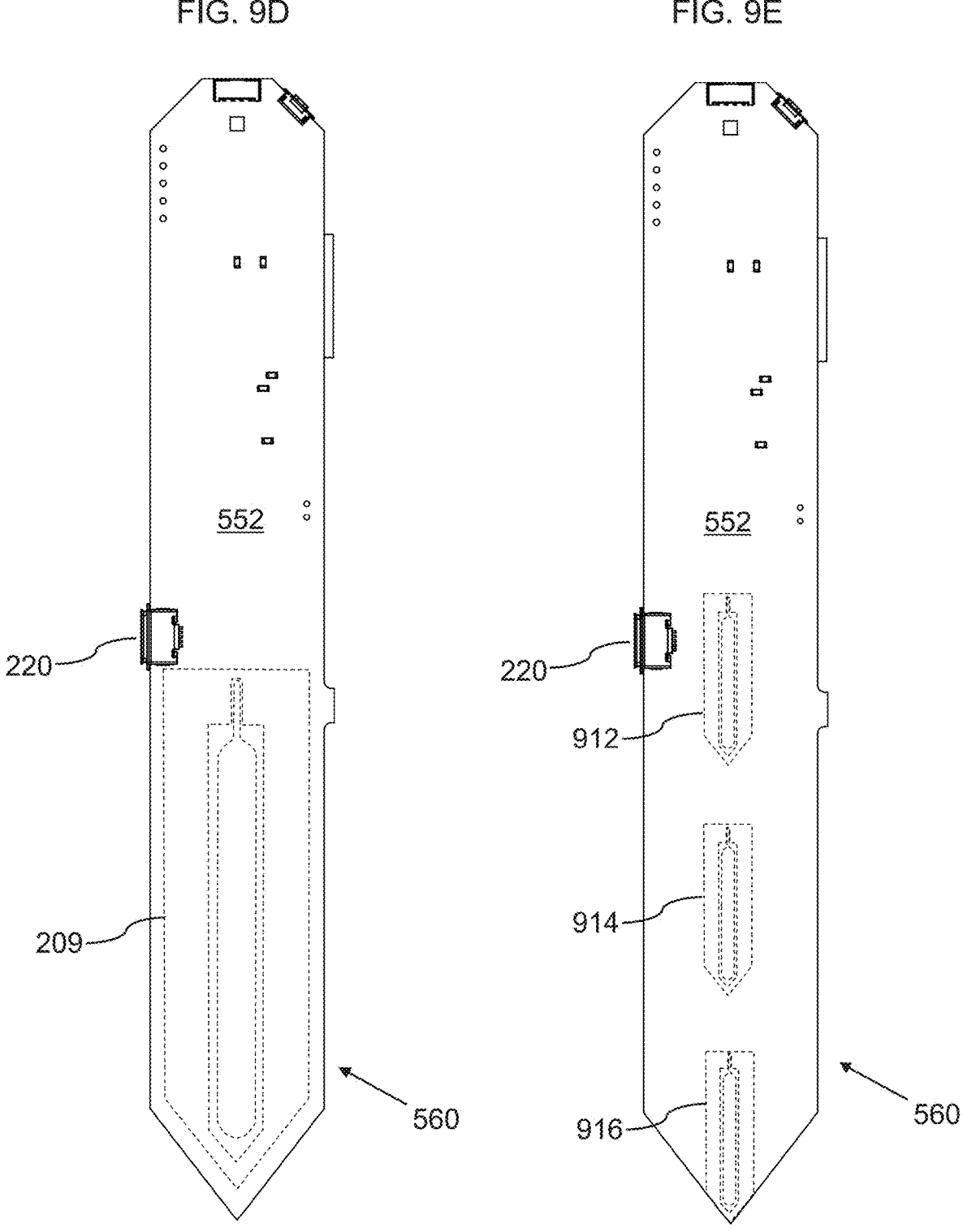
FIG. 9D is a back view of a PCB assembly, according to an embodiment of the invention.
FIG. 9E is a back view of a PCB assembly, according to an embodiment of the invention.

In a further related embodiment, as shown in FIG. 9D, the plant management sensor device 106, can include a moisture sensor probe 209, which can be configured to measure a soil moisture of the planting soil 188.

In another related embodiment, the microcontroller of the plant management sensor device 106, can be used to read sensors measurements of the plant's environment such as: soil moisture, ambient relative humidity, ambient temperature and ambient light.

In yet another related embodiment, the microcontroller of the plant management sensor device 106, can also connect to a Wi-Fi network to send sensor data to a server, where this sensor data can later be shown in a mobile app.

In a related embodiment, the plant management sensor device 106, can include a secure, waterproof sealing for protecting internal electronics.

In a related embodiment, the plant management system 100, can include a system for plant identification, which can include photograph recognition.

In a related embodiment, the plant management system 100, can include a system for user notifications, which can include time-based notifications for plant care.

In a related embodiment, the plant management system 100, can include a system for providing plant care recommendations, which can include recommendations on: light, moisture, humidity, temperature, repotting, and other plant care related states or information.

In a related embodiment, the plant management system 100, can include a system for tracking plant growth, which can include a history for each individual plant.

In another related embodiment, the plant management system 100, can include a social media system for social networking 112, such that the user 116 can create social media posts, which can include photographs, text, and other forms of user interaction.

In a further related embodiment, the plant management system 100, can include a customizable interface and notifications, which can include plant care schedule customization.

In a still further related embodiment, the plant management system 100, can include a system for plant diagnosis, which can include automated or nonautomated plant care recommendations.

In another related embodiment, the plant management system 100, can include guides on plant care, such as for example guides on: repotting, propagation, pruning, misting, and fertilizer guides.

In a related embodiment, the plant management system 100, can include a custom image-labeling, machine-learning enabled model 316, which can use, for example, Google ML Kit.

In another related embodiment, the plant management system 100, can include a plant reference database 312, which can, for example, be a custom database of popular house plants.

In still another related embodiment, the plant reference database 312, can be sorted by popularity, which can be determined by the number of searches for a particular plant, and number of users 116, with a particular plant.

In another related embodiment, the image data of the plant reference database 312, can be scraped for image URLs and can be added to an image-labeling, machine-learning enabled model, through the use of custom scripts.

In yet another related embodiment, the plant reference database 312, can include open-licensed images from online search engines, such as for example, Google™, and can include a plurality of images for each plant, which can be used to train an image-labeling, machine-learning enabled model.

In a further related embodiment, an image-labeling, machine-learning enabled model, can be implemented into a codebase, which can be, for example, Swift iOS codebase, and which can be checked for accuracy and repeated entries.

In a related embodiment, an image-labeling, machine-learning enabled model, can be re-trained based on failure or success.

In still another related embodiment, a plant reference database 312, can be paired with successfully identified images to automatically set a plant management sensor device 106, sensor thresholds for moisture, humidity, temperature, and light.

In a related embodiment, a plant management sensor device 106 sensor thresholds for moisture, humidity, temperature, and light can be used to create upper and lower bounds for the datasets of a plant reference database 312.

In another related embodiment, a plant management sensor device 106 can be configured with sensor thresholds for moisture, humidity, temperature, and light, which can be used to create a model for microclimate learning.

In still another related embodiment, a plant management sensor device 106 can be configured with sensor thresholds for moisture, humidity, temperature, and light, which can be manually adjusted by a user 116.

In a related embodiment, an image-labeling, machine-learning enabled model 316, can be combined with manual inputs such as pot size, soil type, light orientation, and longitudinal/latitudinal location of a user 116, which can further improve the accuracy of the model through a combination of the above inputs and local climate data.

In a related embodiment, local climate data which can improve the accuracy of an image-labeling, machine-learning enabled model 316, can be obtained through the use of an API, such as for example, the OPENWEATHER™ API.

In a related embodiment, an image-labeling, machine-learning enabled model 316, can be trained to make recommendations based on a local climate, which can have increased accuracy by means of an aggregated data set from a plurality of users 116.

In a related embodiment, a stake-like geometry of a PCB main body 552, can be configured to act like a large capacitor, which can take advantage of a parasitic capacitance of two traces placed near each other.

In a related embodiment, the traces of a PCB main body 552, can be made of copper, such as for example an electronic grade copper foil.

In a further related embodiment, a capacitive moisture sensor of a PCB assembly 650, can be designed using a four-layer PCB and can include copper traces in one of the inner copper layers to prevent water from seeping into the copper traces and causing oxidation.

In a related embodiment, the traces of a PCB main body 552, can act like a capacitor through a "parasitic capacitance" effect, which can be exploited to measure changes in the environment.

In a further related embodiment, the capacitance of a capacitor of a made of two traces of a PCB main body 552, can include a plurality of shapes of the traces, which can change its capacitance and charging time.

In another related embodiment, a moisture sensor circuit 208, of an electronics assembly 954, can have a variable charging time.

In another related embodiment, an electronics assembly 954, of a PCB assembly 650, can be used to generate a square wave and detect capacitance charging time.

Figure 9F:
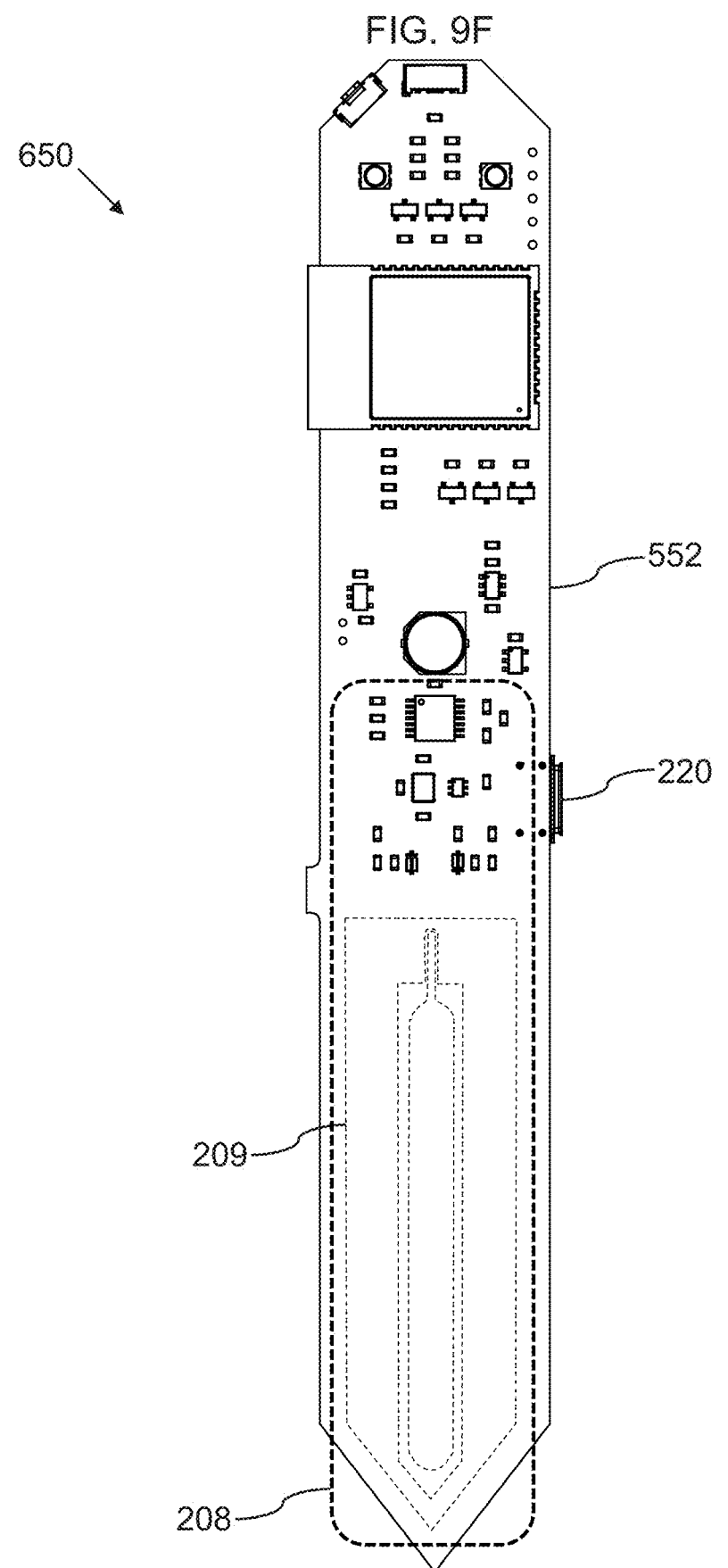
FIG. 9F is a front view of a PCB assembly, according to an embodiment of the invention.

In a related embodiment, as shown in FIG. 9F, a moisture sensor circuit 208, can include an oscillator which can generate a square wave voltage which can be used to charge and discharge a capacitor.

In a related embodiment, as shown in FIGS. 9D and 9F, a moisture sensor circuit 208, can include a copper probe node 209, which can be a probe at a stake-like portion of a PCB main body 552.

In a further related embodiment, as shown in FIGS. 9E-9F, a moisture sensor circuit 208, can include a plurality of moisture probes 912, 914, 916, which can be configured to measure soil moisture at different depths, when the ground spear 560 of the plant management sensor device 106 is inserted into the planting soil 188.

In yet another related embodiment, as shown in FIG. 9F, a moisture sensor circuit 208, can include a quad operational amplifier, which can be used to convert the oscillating signal into an analog voltage that can be read by a main controller 202.

In a further related embodiment, a moisture sensor circuit 208 with a plurality of sensor probes 209, 912, 914, 916 can be implemented with a multiprobe (multipad) capacitive touch sensor, which can resemble a capacitive touch slider used in some commercial products, wherein multiple capacitive touch buttons/pads are used to detect where the user is touching the slider. The multiprobe capacitive touch sensor detects change in capacitance, and because the soil moisture affects the capacitance of the probes, can be used to measure the soil moisture level.

In a related embodiment, a temperature and humidity sensor circuit 210, can include a digital temperature and humidity sensor, which can consist of a capacitive humidity sensor, a bandgap temperature sensor, analog and digital signal processing, A/D converter, calibration data memory, and a digital communication interface.

In another related embodiment, a temperature and humidity sensor circuit 210, can include a humidity measurement range of 0 to 100% RH and a temperature measurement range of −40° C. to 125° C. with a typical accuracy of ±2% RH and ±0.2° C.

In a further related embodiment, a temperature and humidity sensor circuit 210, can include a high accuracy ambient light digital 16-bit resolution sensor which can include a high sensitivity photodiode, a low noise amplifier, a 16-bit A/D converter and which can supports a I2C bus communication interface which can output an ambient light value as a digital value, and which can provide lux readings.

In a related embodiment, a temperature and humidity sensor circuit 210, can operate on a supply voltage of 1.6V to 3.6V with an energy budget below 1 microjoule per measurement.

In a related embodiment, a temperature and humidity sensor circuit 210, can be located on a bottom layer of a PCB main body 552.

In a related embodiment, a light sensor circuit 212, can include an ambient light sensor, which can be, for example, a digital 16-bit resolution sensor, which can be comprised of a high sensitivity photodiode, a low noise amplifier, a 16-bit A/D converter and which can support a I2C bus communication interface.

In a related embodiment, a light sensor circuit 212, can be located on a bottom layer of the PCB main body 552.

In another related embodiment, the plant management server 102 can further include:

a) A plant diagnosis manager, which can include a plant diagnosis model, such that the plant diagnosis manager executes the plant diagnosis model to provide multiple layers of user input, plant specific recommendations and care guides tied to the image classification model of the plant id manager 310, and user-aggregated data to provide diagnoses and solutions for our users. The plant diagnosis model can be implemented as decision tree, which can make decisions based on used input and sensor readings from the sensors 208, 210, 212, 214.

In yet another related embodiment, the plant management server 102 can further include:

a) A carbon offset tracker, which can enable users to automatically track carbon emissions offsets for plants in the plant user database 318.

In a further related embodiment, the carbon offset tracker can calculate carbon emissions offsets based on various factors, including:

a) Specific plant species, wherein the plant reference database 312 can include carbon offset values for each plant reference record 332.

b) Size of the pot and plant; and c) Aggregated user data.

Thus, in an embodiment, as shown in FIG. 1, a plant management system 100 can include:

a) at least one plant management sensor device 106, which can include:

i. a light sensor 212, which is configured to measure a light intensity of ambient light 192;

wherein the plant management sensor device 106 can be configured to be positioned in proximity to at least one plant 182, 184, which is planted in a planting soil;

b) a plant management server 102, which can include:

i. a plant id manager 310, which is configured to identify a plant species 334, based on a plant actual image 492;

ii. a plant reference database 312, which comprises a reference library of plant information, wherein the plant reference database 312 can include:

1. a plurality 330 of plant reference records 332;

wherein the plant id manager 310 can be configured to identify the plant actual image 492 to match a plant reference image 392 of a corresponding plant reference record 332 by a search in the plant reference database 312; and c) a plant management control device 104, which can include:

i. a camera 408, wherein the plant actual image 492 is captured by the camera 408;

ii. a plant controller 410, which is configured to view and process the plant information, received from the plant reference database 312, in communication via the plant management server 102; and such that the plant management control device 104 is configured to enable a user 116 to control and view sensor data, from the at least one plant management sensor device 106.

In a related embodiment, the at least one plant management sensor device 106 can further include:

a) A moisture sensor 208, which is configured to measure a soil moisture of the planting soil 188.

In another related embodiment, the at least one plant management sensor device 106 can further include:

a) a ground spear 560, which is configured be inserted into the planting soil 188;

wherein the moisture sensor 208 comprises at least one moisture probe 209;

wherein the ground spear 560 can include the at least one moisture probe 209.

Figure 2A:
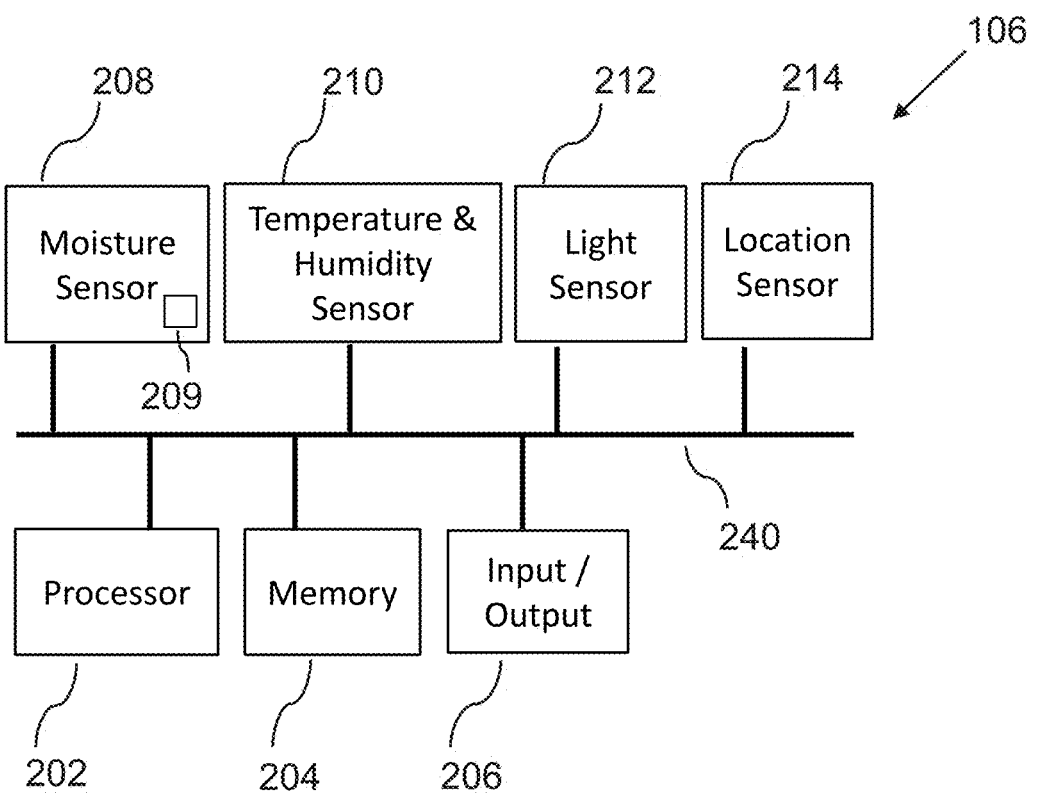
FIG. 2A is a schematic diagram illustrating a plant management sensor device server, according to an embodiment of the invention.
Figure 2B:
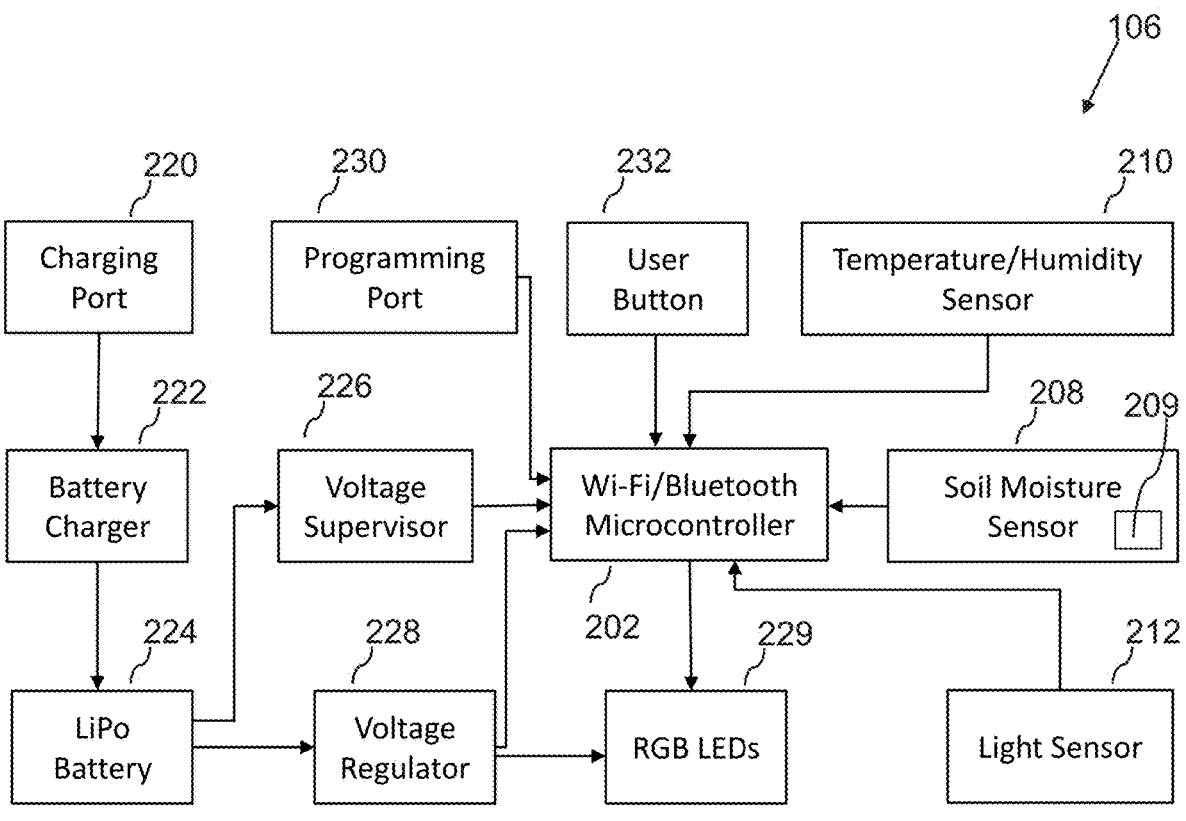
FIG. 2B is a schematic diagram illustrating a plant management sensor device hardware flowchart, according to an embodiment of the invention.

In a further related embodiment, as shown in FIGS. 2A, 9D, and 9E, the at least one moisture probe 209 can further include a plurality, such as two, three (as shown) or more moisture probes 209, which can include:

a) a first moisture probe 912, which is connected to the ground spear 560;

b) a second moisture probe 914, which is connected to the ground spear 560; and c) a third moisture probe 916, which is connected to the ground spear 560;

such that the second moisture probe 914 is mounted below the first moisture probe 912;

such that the third moisture probe 916 is mounted below the second moisture probe 914;

such that the first moisture probe 912 measures a first corresponding moisture at a first depth in the planting soil;

such that the second moisture probe 914 measures a second corresponding moisture at a second depth in the planting soil;

such that the third moisture probe 916 measures a third corresponding moisture at a third depth in the planting soil;

wherein the second depth is larger than the first depth; and wherein the third depth is larger than the second depth.

In another further related embodiment, the at least one plant management sensor device 106 can further include:

a) a printed circuit board 552;

b) a processor 202, which is mounted on the printed circuit board 552; and c) a non-transitory memory 204, which is mounted on the printed circuit board 552;

wherein a lower portion of the printed circuit board 552 is configured as the ground spear 560.

In a related embodiment, the at least one plant management sensor device 106 can further include:

a) a temperature and humidity sensor 210, which is configured to measure an ambient temperature and an ambient humidity.

In yet a related embodiment, the plant management server 102, can further include:

a) a micro-climate manager 314, which is configured to capture, store, and process local climate information received from the at least one plant management sensor device 106.

In a further related embodiment, the plant management control device can further include:

a) a micro-climate controller 412, which is configured to view and process climate information, received from the at least one plant management sensor device 106, in direct communication with at least one of the plant management control device 104, the at least one plant management sensor device 106, and the plant management server 102.

In another further related embodiment, each plant reference record 332 in the plurality 330 of plant reference records 332 can further include:

a) a plant species identifier 334;

b) a plant temperature range 350, which comprises a minimum recommended temperature and a maximum recommended temperature;

c) a plant light exposure range 360, which comprises a minimum recommended light exposure and a maximum recommended light exposure;

d) a plant soil moisture range 372, which comprises a minimum recommended soil moisture and a maximum recommended soil moisture; and e) at least one plant reference image 392.

In a yet further related embodiment, each plant reference record 332 in the plurality 330 of plant reference records 332 can further include:

a) a plant description 340;

b) a plant soil descriptor 370, which can include:

i. the plant soil moisture range 372; and ii. a plant soil type 374; and c) a plant nutrient descriptor 380, which can include:

i. a plant fertilization mix 382; and ii. a plant fertilization quantity 384.

In a related embodiment, the plant management server 102 can further include a plant user database 318, which comprises a user library of plant user information, wherein the plant user database 318 can further include:

a) a plurality 430 of plant user records 432, each plant user record 432 including:

i. a plant user identifier 433, which identifies a plant 106 in the garden bed 180 of the user 116;

ii. a plant reference identifier 434 (which can also be referred to as a plant species identifier 434), which links to a plant species identifier 334 of a plant reference record 332 in the plurality 330 of plant reference records 332 in the plant reference database 312;

iii. a plant location 435;

iv. a sensor identifier 438; and v. a plurality of plant status records 440, each plant status record comprising:

2. a capture time stamp 442, which can include a date and a time; and 3. a plant sensor capture 450, which can include:

a soil moisture measurement 452;

an air temperature measurement 454;

a light intensity measurement 458.

In a further related embodiment, the plant sensor capture 450 can further include:

a) an air humidity measurement 456.

In a related embodiment, each plant user record 432 in the plurality of plant user records 432 can further include:

a) a sensor location 439.

In another related embodiment, the plant management server 102 can further include:

a) a micro-climate model 316;

wherein the micro-climate manager 314 is configured to process a machine learning algorithm for training and executing the micro-climate model 316, such that the micro-climate manager 314 is configured to generate a model output based on a machine learning calculation of a model input on the micro-climate model 316;

wherein the model input comprises: an input time stamp 442 and an input location 435, 439; and wherein the model output comprises: an estimated air temperature and an estimated light intensity.

In a further related embodiment, the model output can further include: an estimated air humidity and an estimated soil moisture.

In another further related embodiment, the micro-climate manager 314 can be configured to train the micro-climate model 316 with each plant user record 432 in the plurality of plant user records 432, such that the micro-climate model 316 is optimized to generate the model output based on the model input.

In various further related embodiments, the machine learning algorithm can use at least one or a combination of well-known methods of machine learning, including artificial neural networks, such as deep learning neural networks with back-propagation learning, deep belief networks, deep reinforcement learning, convolutional neural networks, genetic algorithms; support vector machines, cluster classification, etc.

In yet another further related embodiment, the micro-climate model 316 can be configured as an artificial neural network with at least two hidden layers, such that the micro-climate model is implemented by the optimized/trained artificial neural network, which can be trained/optimized using well-known artificial neural network deep learning algorithms, including backpropagation and other non-linear function optimization methods. In many related embodiments, learning/training can be unsupervised, but in some embodiments, learning may be supervised or partially supervised, and may employ reinforcement learning.

In a related embodiment, at least some plant status records 440 in the plurality of plant status records 440 can further include:

a) a plant size measurement 444;

such that the plant management system 100 can enable the user 116 to track plant growth for each plant 182, 184 in the plant user database 318.

In a further related embodiment, the plant management control device 104 can be configured to enable the user 116 to manually input the plant size measurement 444, such that the plant size measurement 444 is transmitted to the plant management control device 104 for storage in the plant user database 318.

In related embodiments, the plant management control device 104, can include configurations as:

a) A web application, executing in a Web browser;

b) A tablet app, executing on a tablet device, such as for example an ANDROID™ or IOS™ tablet device;

c) A mobile app, executing on a mobile device, such as for example an ANDROID™ phone or IPHONE™, or any wearable mobile device;

d) A desktop application, executing on a personal computer, or similar device; and e) An embedded application, executing on a processing device, such as for example a smart TV, a game console or other system.

It shall be understood that an executing instance of an embodiment of the plant management system 100, as shown in FIG. 1, can include a plurality of plant management control devices 104, which are each tied to one or more users 116.

An executing instance of an embodiment of the system for the plant management system 100, as shown in FIG. 1, can similarly include a plurality of plant management servers 102.

Figure 10A:
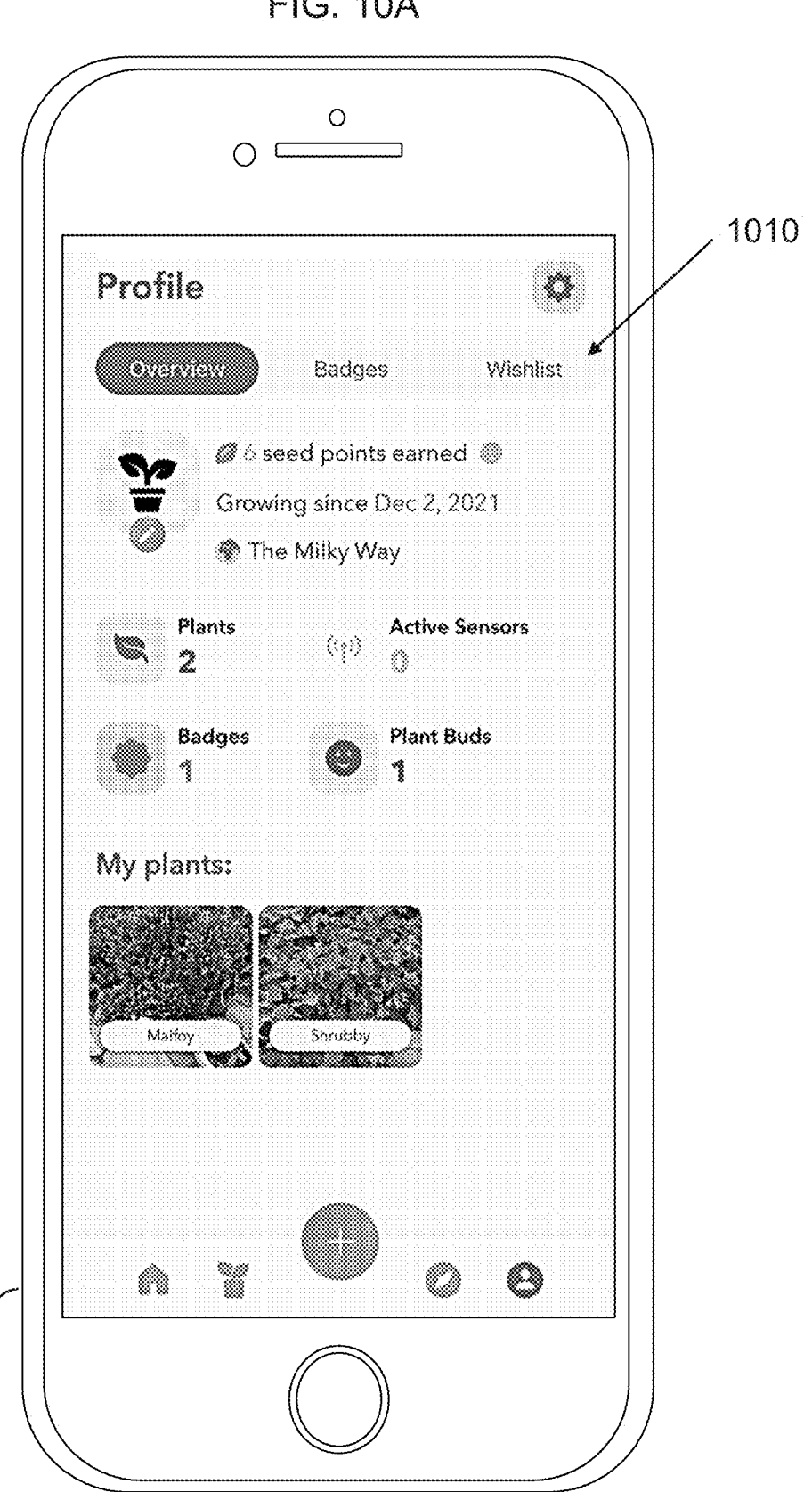
FIG. 10A is an illustration of a profile graphical user interface of the plant management control device, according to an embodiment of the invention.
Figure 10B:
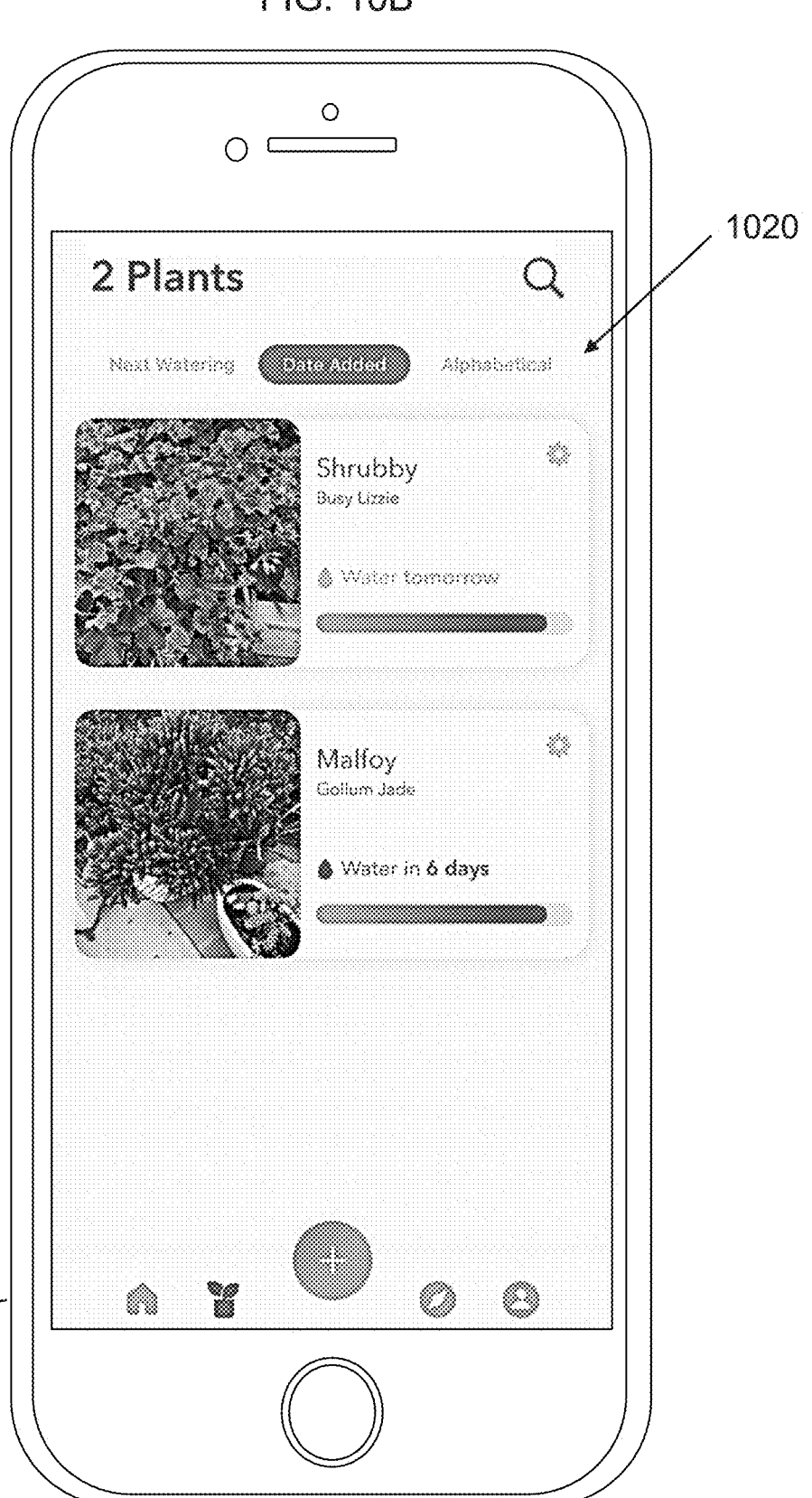
FIG. 10B is an illustration of a plant summary graphical user interface of the plant management control device, according to an embodiment of the invention.

In a related example embodiment, FIG. 10A shows a profile application view/window 1010 associated with the GUI for the plant management control device 104.

In another related example embodiment, FIG. 1013 shows a plant summary application view/window 1020 associated with the GUI for the plant management control device 104.

Figure 10C:
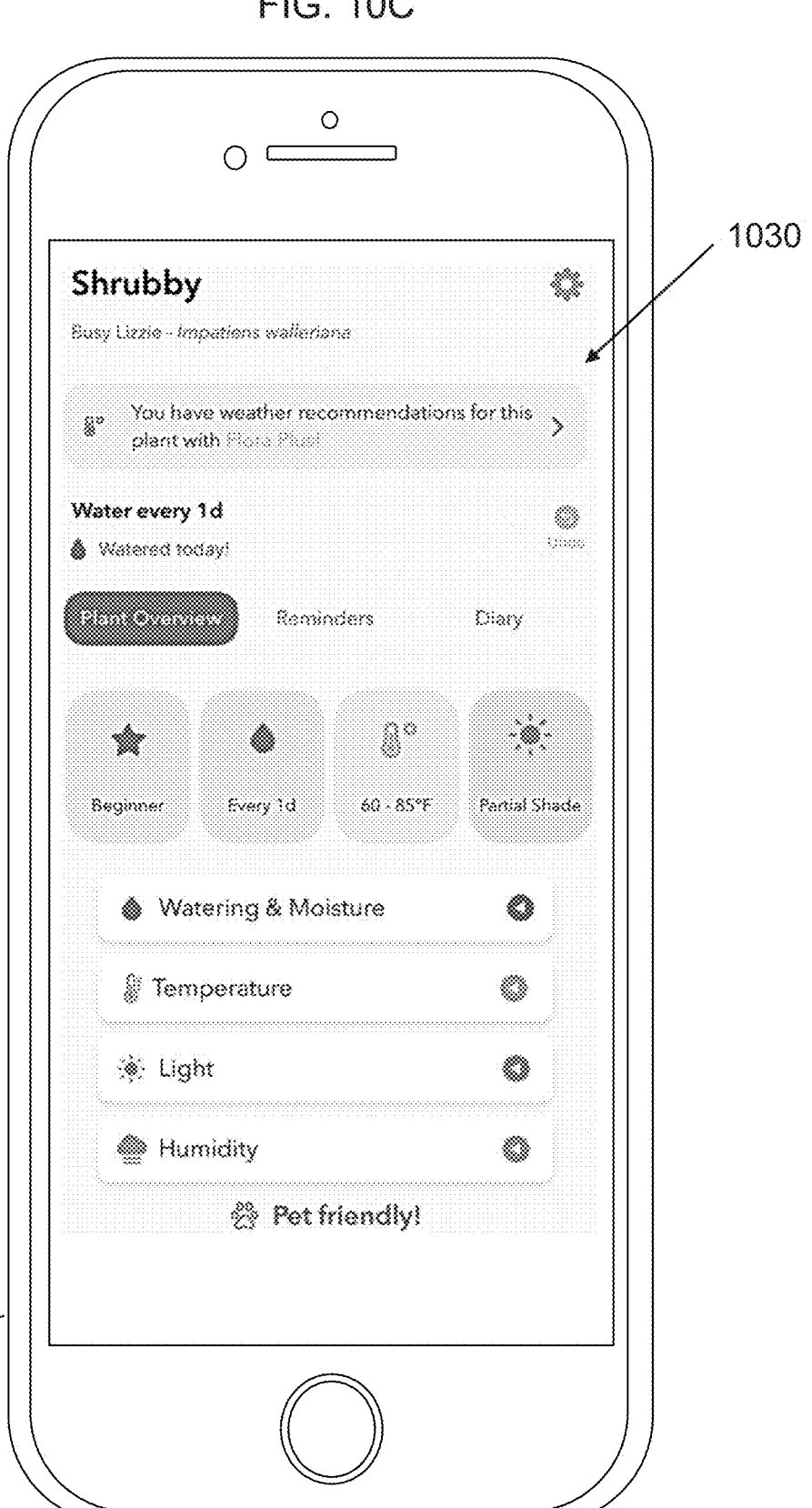
FIG. 10C is an illustration of a first plant detail graphical user interface of the plant management control device, according to an embodiment of the invention.

In yet another related example embodiment, FIG. 10C shows a first plant detail application view/window 1030 associated with the GUI for the plant management control device 104.

Figure 10D:
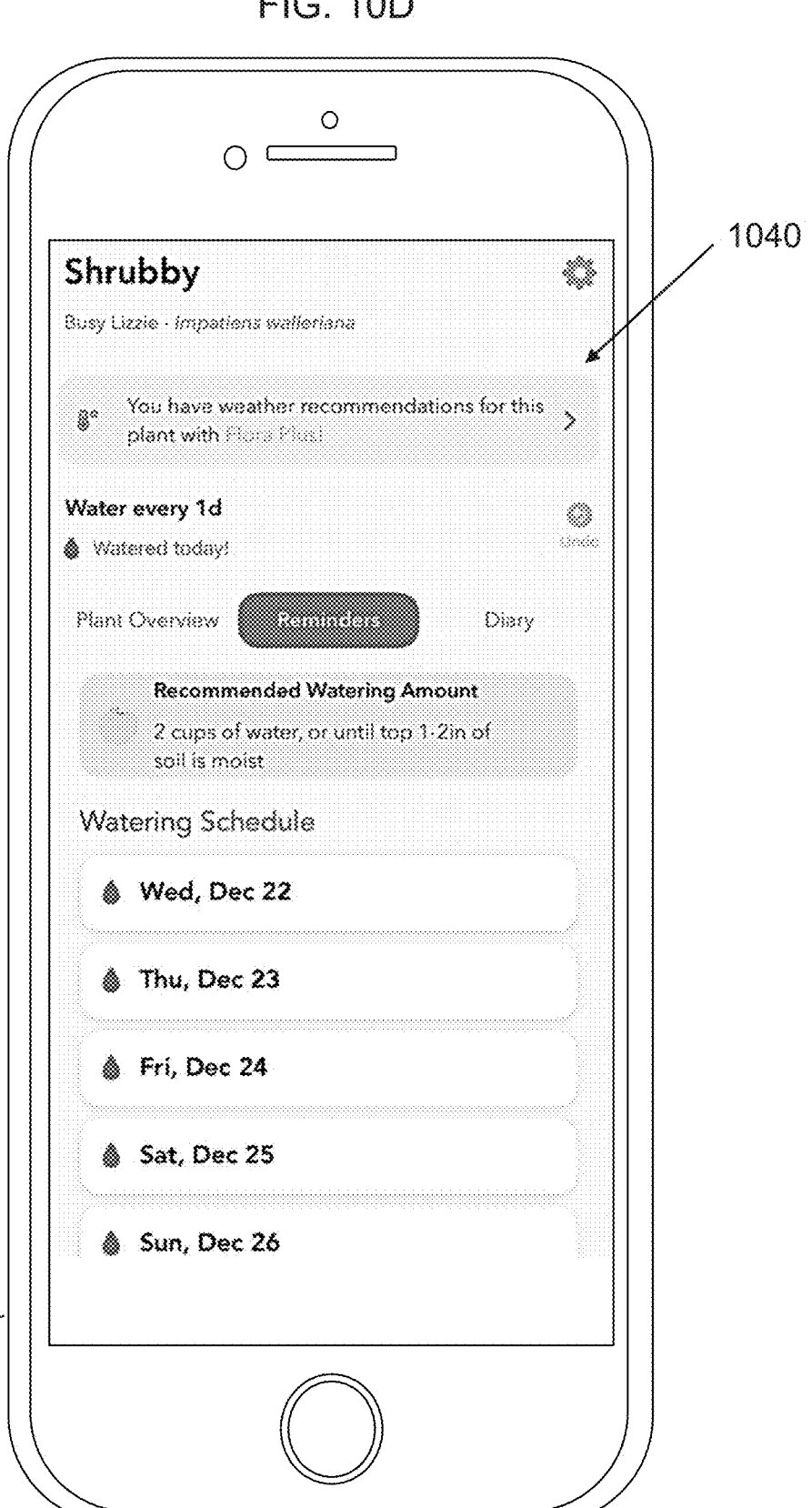
FIG. 10D is an illustration of a second plant detail graphical user interface of the plant management control device, according to an embodiment of the invention.

In a related example embodiment, FIG. 10D shows a second plant detail application view/window 1040 associated with the GUI for the plant management control device 104.

Figure 10E:
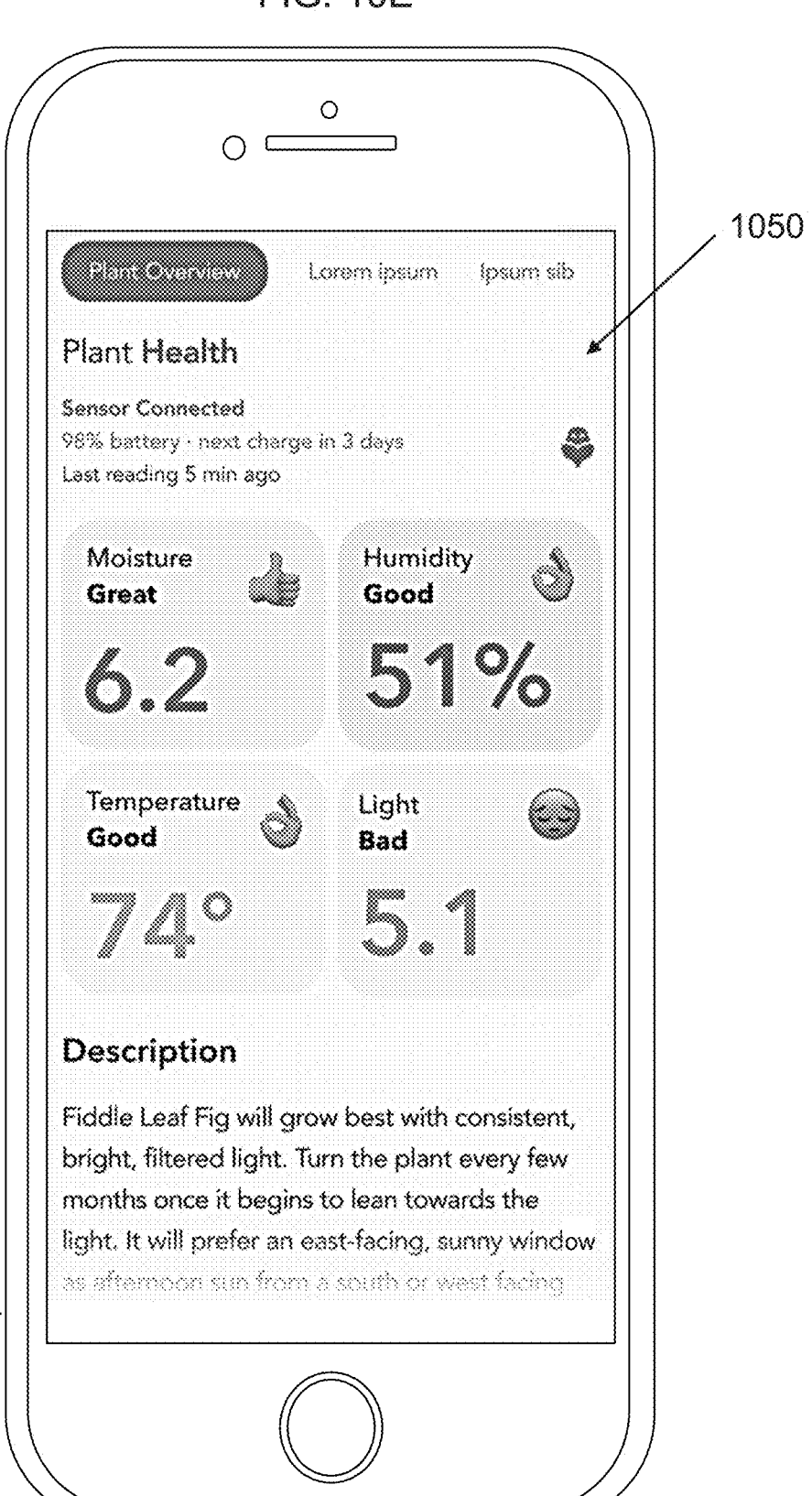
FIG. 10E is an illustration of a plant health overview graphical user interface of the plant management control device, showing sensor readings, according to an embodiment of the invention.

In a related example embodiment, FIG. 10E shows a plant health overview application view/window 1050 associated with the GUI for the plant management control device 104, wherein the plant health overview application view/window 1050 includes sensor readings.

Figure 10F:
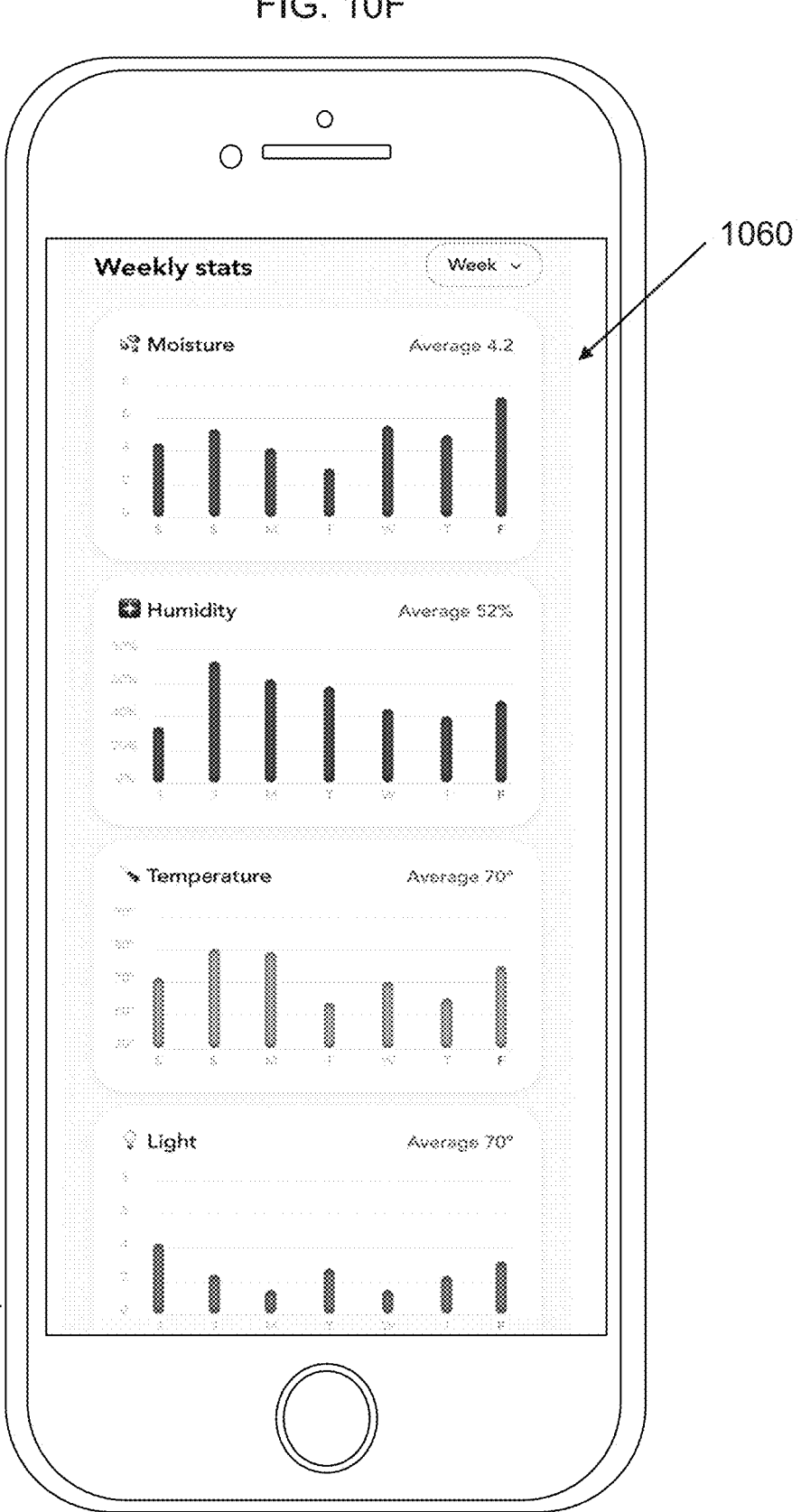
FIG. 10F is an illustration of a plant sensor detail graphical user interface of the plant management control device, showing daily sensor readings, according to an embodiment of the invention.

In a related example embodiment, FIG. 10F shows a plant sensor detail application view/window 1060 associated with the GUI for the plant management control device 104, wherein the plant sensor detail application view/window 1060 includes daily sensor results for the past week.

FIGS. 1, 2A-2B, 3A-3B, and 4 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1, 2A-2B, 3A-3B, and 4 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

FIG. 1 shows a depiction of an embodiment of the plant management system 100, including the plant management server 102, and the plant management control device 104. In this relation, a server shall be understood to represent a general computing capability that can be physically manifested as one, two, or a plurality of individual physical computing devices, located at one or several physical locations. A server can for example be manifested as a shared computational use of one single desktop computer, a dedicated server, a cluster of rack-mounted physical servers, a datacenter, or network of datacenters, each such datacenter containing a plurality of physical servers, or a computing cloud, such as AMAZON EC2™ or MICROSOFT AZURE™.

It shall be understood that the above-mentioned components of the plant management server 102, and the plant management control device 104 are to be interpreted in the most general manner.

For example, the processors 202, 302, 402 can each respectively include a single physical microprocessor or microcontroller, a cluster of processors, a datacenter or a cluster of datacenters, a computing cloud service, and the like.

In a further example, the non-transitory memory 204, 304, 404 can include various forms of non-transitory storage media, including random access memory and other forms of dynamic storage, and hard disks, hard disk clusters, cloud storage services, and other forms of long-term storage. Similarly, the input/output 206, 306, 406 can include a plurality of well-known input/output devices, such as screens, keyboards, pointing devices, motion trackers, communication ports, and so forth.

Furthermore, it shall be understood that the plant management server 102, the plant management control device 104, and the plant management sensor device 106 can each respectively include a number of other components that are well known in the art of general computer devices, and therefore shall not be further described herein. This can include system access to common functions and hardware, such as for example via operating system layers such as WINDOWS™, LINUX™, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user 116, to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the plant management control device 104 and the plant management sensor device 106 each communicate with the plant management server 102, over a network 108, which can include the general Internet, a Wide Area Network or a Local Area Network, or another form of communication network, transmitted on wired or wireless connections, such as for example Ethernet, Wi-Fi, BLUETOOTH™, ZIGBEE™, and NFC.

In a related embodiment, the communication of the plant management control device 104 and the plant management sensor device 106, with the plant management server 102, over a network 108, can be via a secure, encrypted communication protocol.

In various related embodiment, as shown in FIGS. 2A, 2B, 3A, and 4, components of the plant management sensor device 106, the plant management server 102, and the plant management control device 104 can include:

a) Software modules 310, 314, 410, 412, which can include the plant id manager 310, the micro-climate manager 314, the plant controller 410, and the micro-climate controller 412;

wherein the software modules 310, 314, 410, 412 are denoted in FIGS. 2A, 2B, 3A, and 4 by soft/rounded corner rectangles, and wherein the software modules 310, 314, 410, 412 can be defined by computer program instructions for execution by a processor 202, 302, 402; and b) Hardware components 202, 302, 402, 204, 304, 404, 206, 306, 406, 208, 408, which can for example include a processor 202, 302, 402, a non-transitory memory 204, 304, 404, an input/output component 206, 306, 406, a moisture sensor 208, a camera 408, etc., etc.;

wherein the Hardware components 202, 302, 402, 204, 304, 404, 206, 306, 406, 208, 408 are denoted in FIGS. 2A, 2B, 3A, and 4 by hard corner rectangles, and can be defined by circuits in silicone and/or other materials and can be mounted on a circuit board.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the plant management system 100, including the plant management server 102, the plant management sensor device 106, and the plant management control device 104, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

For example, alternative embodiments can reconfigure or combine the components of the plant management server 102, the plant management sensor device 106, and the plant management control device 104. The components of the plant management server 102, can be distributed over a plurality of physical, logical, or virtual servers. Parts or all of the components of the plant management control device 104, can be configured to operate in the plant management server 102, whereby the plant management control device 104, for example can function as a thin client, performing only graphical user interface presentation and input/output functions. Alternatively, parts or all of the components of the plant management server 102, can be configured to operate in the plant management control device 104.

Many such alternative configurations are readily apparent, and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A plant management system, comprising:

a) at least one plant management sensor device, comprising:

a light sensor, which is configured to measure a light intensity of ambient light;

wherein the plant management sensor device is configured to be positioned in proximity to at least one plant, which is planted in a planting soil;

b) a plant management server, comprising:

a plant id manager, which is configured to identify a plant species, based on a plant actual image;

a plant reference database, which comprises a reference library of plant information, wherein the plant reference database comprises:

a plurality of plant reference records, wherein each plant reference record in the plurality of plant reference records comprises:

a plant species identifier;

a plant temperature range, which comprises a minimum recommended temperature and a maximum recommended temperature;

a plant light exposure range, which comprises a minimum recommended light exposure and a maximum recommended light exposure;

a plant soil moisture range, which comprises a minimum recommended soil moisture and a maximum recommended soil moisture; and at least one plant reference image; and a micro-climate manager, which is configured to capture, store, and process local climate information received from the at least one plant management sensor device;

wherein the plant id manager is configured to identify the plant actual image to match a plant reference image of a corresponding plant reference record by a search in the plant reference database; and c) a plant management control device, comprising:
a camera, wherein the plant actual image is captured by the camera; and
a plant controller, which is configured to view and process the plant information, received from the plant reference database, in communication via the plant management server; and
such that the plant management control device is configured to enable a user to control and view sensor data, from the at least one plant management sensor device.

2. The plant management system of claim 1, wherein the plant management server, further comprises:
a plant user database, which comprises a user library of plant user information, wherein the plant user database comprises:
a plurality of plant user records, each comprising:
a plant user identifier, which identifies the at least one plant;
a plant reference identifier, which links to the plant species identifier of a plant reference record in the plurality of plant reference records in the plant reference database; and
a sensor identifier; and
a plurality of plant status records, each comprising:
a capture time stamp, comprising a date and a time; and
a plant sensor capture, comprising:
a soil moisture measurement;
an air temperature measurement; and
a light intensity measurement.

3. The plant management system of claim 2, wherein the plant sensor capture further comprises:
an air humidity measurement.

4. The plant management system of claim 2, wherein each plant user record in the plurality of plant user records further comprises:
a plant location.

5. The plant management system of claim 4, wherein the plant management server, further comprises:
a micro-climate model;
wherein the micro-climate manager is configured to process a machine learning algorithm for training and executing the micro-climate model, such that the micro-climate manager is configured to generate a model output based on a machine learning calculation of a model input on the micro-climate model, wherein the model input comprises: an input time stamp and an input location;
wherein the model output comprises: an estimated air temperature and an estimated light intensity.

6. The plant management system of claim 5, wherein the model output further comprises: an estimated air humidity and an estimated soil moisture.

7. The plant management system of claim 5, wherein the micro-climate manager is configured to train the micro-climate model with each plant user record in the plurality of plant user records, such that the micro-climate model is optimized to generate the model output based on the model input.

8. The plant management system of claim 5, wherein the micro-climate model is an artificial neural network with at least two hidden layers.

9. The plant management system of claim 2, wherein at least some plant status records in the plurality of plant status records, further comprises:
a plant size measurement;
such that the plant management system is configured to enable the user to track plant growth for each plant in the plant user database.

10. The plant management system of claim 9, wherein the plant management control device is configured to enable the user to manually input the plant size measurement, such that the plant size measurement is transmitted to the plant management control device for storage in the plant user database.

11. The plant management system of claim 1, wherein the at least one plant management sensor device further comprises:
a moisture sensor, which is configured to measure a soil moisture of the planting soil.

12. The plant management system of claim 11, wherein the at least one plant management sensor device further comprises:
a ground spear, which is configured be inserted into the planting soil;
wherein the moisture sensor comprises at least one moisture probe;
wherein the at least one moisture probe is connected to the ground spear.

13. The plant management system of claim 12, wherein the at least one moisture probe comprises:
a) a first moisture probe, which is connected to the ground spear; and
b) a second moisture probe, which is connected to the ground spear;
such that the second moisture probe is mounted below the first moisture probe;
such that the first moisture probe measures a first corresponding moisture at a first depth in the planting soil; and
such that the second moisture probe measures a second corresponding moisture at a second depth in the planting soil;
wherein the second depth is larger than the first depth.

14. The plant management system of claim 12, wherein the at least one plant management sensor device further comprises:
a) a printed circuit board;
b) a processor, which is mounted on the printed circuit board; and
c) a non-transitory memory, which is mounted on the printed circuit board;
wherein a lower portion of the printed circuit board is configured as the ground spear.

15. The plant management system of claim 1, wherein the at least one plant management sensor device further comprises:
a temperature and humidity sensor, which is configured to measure an ambient temperature and an ambient humidity.

16. The plant management system of claim 1, wherein the plant management control device, further comprises:
a micro-climate controller, which is configured to view and process climate information, received from the at least one plant management sensor device, in direct communication with at least one of the plant management control device, the at least one plant management sensor device, and the plant management server.

17. The plant management system of claim 1, wherein each plant reference record in the plurality of plant reference records further comprises:
a) a plant soil descriptor, which comprises:
the plant soil moisture range; and
a plant soil type; and
b) a plant nutrient descriptor, which comprises:
a plant fertilization mix; and
a plant fertilization quantity.

18. The plant management system of claim 1, wherein each plant reference record in the plurality of plant reference records further comprises:
a plant description.

19. A plant management system, comprising:
a) at least one plant management sensor device, comprising:
a light sensor, which is configured to measure a light intensity of ambient light;
wherein the plant management sensor device is configured to be positioned in proximity to at least one plant, which is planted in a planting soil; and
b) a plant management server, comprising:
a plant id manager, which is configured to identify a plant species, based on a plant actual image;
a plant reference database, which comprises a reference library of plant information, wherein the plant reference database comprises:
a plurality of plant reference records, wherein each plant reference record in the plurality of plant reference records comprises:
a plant species identifier;
a plant temperature range, which comprises a minimum recommended temperature and a maximum recommended temperature;
a plant light exposure range, which comprises a minimum recommended light exposure and a maximum recommended light exposure;
a plant soil moisture range, which comprises a minimum recommended soil moisture and a maximum recommended soil moisture; and
at least one plant reference image; and
a micro-climate manager, which is configured to capture, store, and process local climate information received from the at least one plant management sensor device;
wherein the plant id manager is configured to identify the plant actual image to match a plant reference image of a corresponding plant reference record by a search in the plant reference database.

20. The plant management system of claim 19, wherein the plant management server, further comprises:
a plant user database, which comprises a user library of plant user information, wherein the plant user database comprises:
a plurality of plant user records, each comprising:
a plant user identifier, which identifies the at least one plant;

a plant reference identifier, which links to the plant species identifier of a plant reference record in the plurality of plant reference records in the plant reference database; and
a sensor identifier; and
a plurality of plant status records, each comprising:
a capture time stamp, comprising a date and a time; and
a plant sensor capture, comprising:
a soil moisture measurement;
an air temperature measurement; and
a light intensity measurement.

21. The plant management system of claim 20, wherein each plant user record in the plurality of plant user records further comprises:
a plant location.

22. The plant management system of claim 21, wherein the plant management server, further comprises:
a micro-climate model;
wherein the micro-climate manager is configured to process a machine learning algorithm for training and executing the micro-climate model, such that the micro-climate manager is configured to generate a model output based on a machine learning calculation of a model input on the micro-climate model, wherein the model input comprises: an input time stamp and an input location;
wherein the model output comprises: an estimated air temperature and an estimated light intensity.

23. The plant management system of claim 22, wherein the micro-climate manager is configured to train the micro-climate model with each plant user record in the plurality of plant user records, such that the micro-climate model is optimized to generate the model output based on the model input.

24. The plant management system of claim 19, wherein the at least one plant management sensor device further comprises:
a moisture sensor, which is configured to measure a soil moisture of the planting soil.

25. The plant management system of claim 24, wherein the at least one plant management sensor device further comprises:
a ground spear, which is configured be inserted into the planting soil;
wherein the moisture sensor comprises at least one moisture probe;
wherein the at least one moisture probe is connected to the ground spear.

26. The plant management system of claim 19, wherein each plant reference record in the plurality of plant reference records further comprises:
a) a plant soil descriptor, which comprises:
the plant soil moisture range; and
a plant soil type; and
b) a plant nutrient descriptor, which comprises:
a plant fertilization mix; and
a plant fertilization quantity.

* * * * *